(12) United States Patent
Balog et al.

(10) Patent No.: US 7,776,859 B2
(45) Date of Patent: Aug. 17, 2010

(54) HEXAHYDROIMIDAZOPYRAZIN-3-ONE COMPOUNDS USEFUL AS MODULATORS OF ANDROGEN RECEPTOR FUNCTION

(75) Inventors: James Aaron Balog, Lambertville, NJ (US); Mark E. Salvati, Lawrenceville, NJ (US); Brian E. Fink, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 706 days.

(21) Appl. No.: 11/546,965

(22) Filed: Oct. 12, 2006

(65) Prior Publication Data
US 2007/0088039 A1   Apr. 19, 2007

Related U.S. Application Data

(60) Provisional application No. 60/726,672, filed on Oct. 14, 2005.

(51) Int. Cl.
*A61K 31/4985* (2006.01)
(52) U.S. Cl. .................... 514/249; 544/350
(58) Field of Classification Search ............... 544/350
See application file for complete search history.

(56) References Cited

U.S. PATENT DOCUMENTS 7,087,636 B2    8/2006   Salvati et al.
7,141,578 B2   11/2006   Salvati et al.

OTHER PUBLICATIONS

Mahmud et al. "Prostate cancer and use of nonsteroidal anti-inflammatory drugs: systematic review and meta-analysis" 2004,British Journal of Cancer,90,93-99.*
Omodei-Salé, A. et al., "Hexahydroimidazo[1,5-a]pyrazine. I. Synthesis of 7-methyl-1,5,6,7,8a-hexahydroimidazo[1,5-a]pyrazin-3(2H)-one and derivatives", Il Farmaco—Ed. Scient., vol. 30, No. 8, pp. 650-665 (1975), (English Abstract only).
Toja, E. et al., "Hexahydroimidazo[1,5-a]-pyrazine. II. Synthesis of 7-phenyl-1,5,6,7,8,8a-hexahydroimidazo[1,5-a]pyrazine-3(2H)-one and derivatives", Il Farmaco—Ed. Scient., vol. 39, No. 5, pp. 450-462 (1984), (English Abstract only).
Omodei-Salé, A. et al., "Hexahydroimidazo[1,5-a]pyrazine. I. Synthesis of 7-methyl-1,5,6,7,8a-hexahydroimidazo[1,5-a]pyrazin-3(2H)-one and derivatives", Il Farmaco—Ed. Sc.., vol. 30, No. 8, pp. 650-665 (1975), English Translation.

* cited by examiner

*Primary Examiner*—James O Wilson
*Assistant Examiner*—Brian McDowell
(74) *Attorney, Agent, or Firm*—Gary D. Greenblatt; Anastasia P. Winslow

(57) ABSTRACT

The present invention is directed to compounds having the formula (I),

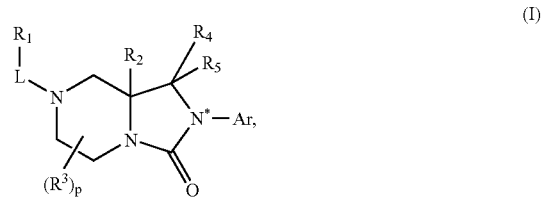

and/or pharmaceutically-acceptable salts thereof, useful in the treatment of androgen-receptor associated conditions, wherein Ar is aryl, substituted aryl, heteroaryl, or substituted heteroaryl; L is a linker as defined in the specification; $R_1$ may be hydrogen, cyano, alkyl, substituted alkyl, aryl, substituted aryl, cycloalkyl, substituted cycloalkyl, heterocyclo, substituted heterocyclo, heteroaryl, or substituted heteroaryl, as defined in the specification; $R_2$ is hydrogen, lower alkyl, or substituted lower alkyl; and $R_3$, $R_4$ and $R_5$ are optionally non-interfering substituents as defined in the specification.

17 Claims, No Drawings

HEXAHYDROIMIDAZOPYRAZIN-3-ONE COMPOUNDS USEFUL AS MODULATORS OF ANDROGEN RECEPTOR FUNCTION

CROSS-REFERENCE TO RELATED APPLICATION

This application claims the benefit of U.S. Provisional Application Ser. No. 60/726,672, filed Oct. 14, 2005, the contents of which are hereby incorporated by reference in its entirety.

FIELD OF THE INVENTION

The present invention relates to hexahydroimidazo[1,5-a]pyrazin-3(5h)-one compounds, to methods of using such compounds in the treatment of androgen receptor-associated conditions such as cancer, and to pharmaceutical compositions containing the compounds.

BACKGROUND OF THE INVENTION

Carcinoma of the prostate (CaP) is the second leading cause of cancer-related death in men. Reportedly, there were an estimated 221,000 new cases of CaP diagnosed in 2003 with an estimated 28,900 deaths. See American Cancer Society, Key Statistics about Prostate Cancer 2003; Jemal et al., CA Cancer J. Clin. Vol. 52 (2002), at p. 23-47. CaP presents a relatively high rate of morbidity and morality necessitating prompt detection and effective treatment.

CaP has been commonly treated with surgery, i.e., radial prostatectomy. This procedure presents drawbacks in terms of surgical risks and impairment, and additionally, its usefulness may be limited to early-stage, organ-confined cancers. In advanced cases, the cancer may have spread beyond the bounds of the removed tissue, making it unlikely surgery will be a successful treatment. Radiation therapy also has been widely used as an alternative and/or supplement to surgery but with limited success.

In recent years, various treatment strategies have focused on inhibiting the role of androgens [testosterone (T) and dihydrotestosterone (DHT)] in prostate tumor growth. The androgen receptor (AR) is a ligand-binding transcription factor in the nuclear-hormone receptor (NHR) superfamily, and it is an important mediator of prostate cancer development and growth. The androgens (T and DHT) compete for binding to the AR (DHT having a higher binding affinity than T), and both T and DHT activate the AR, influencing cell function and stimulating growth of the prostate and other tissues, including prostate tumor cells.

Recent efforts for treating CaP have focused on developing compounds that act as androgen receptor modulators. A compound that binds to the AR and mimics the effect of the natural ligand (e.g., T or DHT) is referred to as an "agonist," while a compound that inhibits the effect of a natural ligand in binding to the AR is referred to as an "antagonist." AR antagonists and/or agonists (collectively, "antiandrogens") have proven useful in the treatment of CaP.

However, AR is related to others members of the subfamily of NHR's, which share a sequence homology to one another. Other members of this sub-family include the estrogen receptor (ER), the progesterone receptor (PR), the glucocorticoid receptor (GR), the mineralocorticoid receptor (MR), and the aldosterone receptor (ALDR). Ligands to these receptors are known to play an important role in the health of men and women. Given the similarity in sequence homology of these NHR's, the development of compounds which have good specificity for one or more steroid receptors, but which have reduced or no cross-reactivity for other steroid receptors (thus reducing or avoiding undesirable side effects), has presented challenges.

There are several known, approved non-steroidal antiandrogens including CASODEX™ (bicalutamide), FLUTAMIDE™ (Eulexin), and NILUTAMIDE™ (Anandrone). However, these antiandrogens may bind reversibly to the AR, and if treatment is continued for a period of years, tumors may become androgen independent. Androgen-independent tumors are not affected by the natural ligands (T and DHT), and thus, antiandrogens may lose effectiveness in treating androgen-independent tumors.

As may be appreciated, there remains a need for more potent AR antagonists and/or AR antagonists with a different pharmacological profile as compared with currently-known antiandrogens.

SUMMARY OF THE INVENTION

According to one aspect of the invention, there are provided compounds having the formula (I),

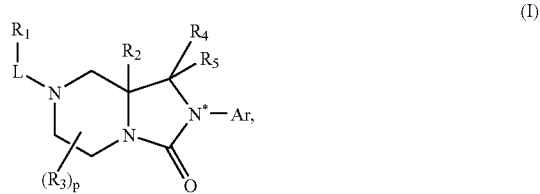

and/or pharmaceutically-acceptable salts thereof, wherein:

Ar is aryl, substituted aryl, heteroaryl, or substituted heteroaryl, wherein Ar is attached to the N* atom of the core ring via a carbon atom of Ar;

L is $-A_1-N(R_{10})C(=O)-A_2-$, $-A_1-C(=O)N(R_{10})-A_2-$, $-A_1-C(=O)-A_2-$, $-A_1-C(=O)O-A_2-$, $-A_1-OC(=O)-A_2-$, $-A_1-C(=NR_{11})-A_2-$, $-A_1-C(=NR_{11})N(R_{10})-A_2-$, $-A_1-S-A_2-$, $-A_1-NR_{10}-A_2-$, $-A_1-S(O)_2-A_2-$, $-A_1-N(R_{10})S(O)_2-A_2-$, $-A_1-S(O)_2N(R_{10})-A_2-$, or $-A_1-A_2-$;

$A_1$ is $-CR_6R_7)_m-$;

$A_2$ is $-CR_8R_9)_n-$;

$R_1$ is hydrogen, alkyl, substituted alkyl, aryl, substituted aryl, cycloalkyl, substituted cycloalkyl, heterocyclo, substituted heterocyclo, heteroaryl, or substituted heteroaryl, or when L is $-A_1-A_2-$ or when m is greater than 0, $R_1$ may be cyano;

$R_2$ is hydrogen, lower alkyl, or substituted lower alkyl;

$R_3$ is at each occurrence individually selected from non-interfering substituents optionally attached at any available carbon atom of the tetrahydropyrazine ring, and two $R_3$ groups attached to the same carbon atom optionally may be taken together to form a carbonyl group;

$R_4$ and $R_5$ are individually selected from hydrogen and non-interfering substituents;

$R_6$, $R_7$, $R_8$, $R_9$ and $R_{10}$ are independently selected from hydrogen, lower alkyl, and substituted lower alkyl;

$R_{11}$ is hydrogen, cyano, or $-OR_{10}$;

m and n are each independently 0 to 6; and p is 0 to 6;

with the proviso, however, that compounds having the formula,

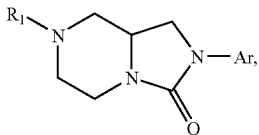

wherein $R_1$ is methyl or unsubstituted phenyl; Ar is

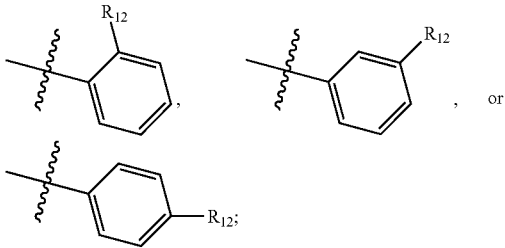

and $R_{12}$ is hydrogen, methyl, chloride, or methoxy; are excluded.

According to another aspect of the invention, there are provided methods of modulating the AR and/or methods of treating AR-associated conditions such as cancer, comprising administering to a patient an effective amount of a compound having the formula (I),

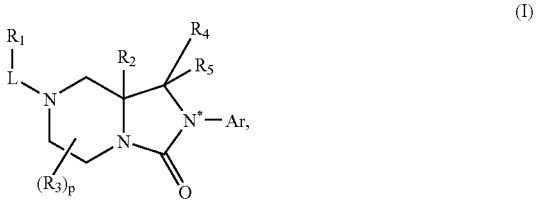

(I)

and/or pharmaceutically-acceptable salts thereof, wherein:

Ar is aryl, substituted aryl, heteroaryl, or substituted heteroaryl, wherein Ar is attached to the N* atom of the core ring via a carbon atom of Ar;

L is -$A_1$-N($R_{10}$)C(=O)-$A_2$-, -$A_1$-C(=O)N($R_{10}$)-$A_2$-, -$A_1$-C(=O)-$A_2$-, -$A_1$-C(=O)O-$A_2$-, -$A_1$-OC(=O)-$A_2$-, -$A_1$-C(=NR$_{11}$)-$A_2$-, -$A_1$-C(=NR$_{11}$)N($R_{10}$)-$A_2$-, -$A_1$-S-$A_2$-, -$A_1$-NR$_{10}$-$A_2$-, -$A_1$-S(O)$_2$-$A_2$-, -$A_1$-N($R_{10}$)S(O)$_2$-$A_2$-, -$A_1$-S(O)$_2$N($R_{10}$)-$A_2$-, or -$A_1$-$A_2$-;

$A_1$ is —$CR_6R_7)_m$—;

$A_2$ is —$CR_8R_9)_n$—;

$R_1$ is hydrogen, alkyl, substituted alkyl, aryl, substituted aryl, cycloalkyl, substituted cycloalkyl, heterocyclo, substituted heterocyclo, heteroaryl, or substituted heteroaryl, or when L is -$A_1$-$A_2$- or when m is greater than 0, $R_1$ may be cyano;

$R_2$ is hydrogen, lower alkyl, or substituted lower alkyl;

$R_3$ is at each occurrence individually selected from non-interfering substituents optionally attached at any available carbon atom of the tetrahydropyrazine ring, and two $R_3$ groups attached to the same carbon atom optionally may be taken together to form a carbonyl group;

$R_4$ and $R_5$ are selected from hydrogen and non-interfering substituents;

$R_6$, $R_7$, $R_8$, $R_9$ and $R_{10}$ are independently selected from hydrogen, lower alkyl, and substituted lower alkyl;

$R_{11}$ is hydrogen, cyano, or —OR$_{10}$;

m and n are each independently 0 to 6; and p is 0 to 6.

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refer to a straight or branched chain alkane (hydrocarbon) radical containing from 1 to 10 carbon atoms, preferably 1 to 6 carbon atoms, more preferably from 1 to 4 carbon atoms. Exemplary such groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, and the like. "Lower alkyl" means a straight or branched chain alkyl having one to four carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms, and the term "$C_{1-4}$alkyl" means alkyl groups of 1 to 4 carbon atoms.

When the term alkyl is used in connection with another group, as in heterocycloalkyl or cycloalkylalkyl, this means the other identified (first named) group is bonded directly through an alkyl group as defined above (e.g., which may be branched or straight chain). Thus, the term "alkyl" is used in this instance to refer to an alkylene, e.g., a divalent alkyl group, having two available points of attachment. For example, cyclopropyl$C_{1-4}$alkyl means a cyclopropyl group bonded through a straight or branched chain alkylene having one to four carbon atoms, and hydroxyalkyl means the group OH bonded through a straight or branched chain alkylene having one to ten carbon atoms, preferably 1 to 6 carbon atoms, more preferably 1 to 4 carbon atoms. In the case of substituents, as in "substituted cycloalkylalkyl," the alkylene portion of the group, besides being branched or straight chain, may be substituted as recited below for substituted alkyl groups and/or the first named group (e.g., cycloalkyl) may be substituted as recited herein for that named group (e.g., in this example cycloalkyl).

"Substituted alkyl" refers to an alkyl group substituted with one or more substituents, preferably 1 to 4 substituents, at any available point of attachment. However, when an alkyl group is substituted with multiple halo substituents, the alkyl may contain as valence allows 1 to 3 non-halo substituents and overall up to 10 substituents (seven to nine halo substituents), more preferably up to seven halo substituents. Alkyl substituents may include one or more of the following groups: halo, haloalkyl, cyano, —OR$_a$, —SR$_a$, —C(=O)R$_a$, —C(=O)OR$_a$, —OC(=O)R$_a$, —OC(=O)OR$_a$, —NR$_a$R$_b$, —C(=O)NR$_a$R$_b$, —OC(=O)NR$_a$R$_b$, —S(=O)R$_a$, —S(O)$_2$R$_a$, —NHS(O)$_2$R$_a$, —NHS(O)$_2$NHR$_a$, —NHC(=O)NHR$_a$, —NHC(=O)R$_a$, —NHC(O)$_2$R$_a$, —NHC(=N—CN)R$_a$, aryl, heterocycle, cycloalkyl, and/or heteroaryl, wherein the groups $R_a$ and $R_b$ are independently selected from hydrogen, alkyl, alkenyl, cycloalkyl, heterocyclo, aryl, and heteroaryl, and wherein each $R_a$ and/or $R_b$ in turn is optionally substituted with one to four groups selected from alkyl, alkenyl, halogen, haloalkyl, haloalkoxy, cyano, nitro, amino, alkylamino, aminoalkyl, hydroxy, hydroxyalkyl, alkoxy, thiol, alkylthio, phenyl, benzyl, phenyloxy, benzyloxy, $C_{3-7}$cycloalkyl, five or six membered heterocyclo or heteroaryl, and/or a lower alkyl or lower alkenyl substituted with one to four groups selected from hydroxy, cyano, halogen, haloC$_{1-4}$ alkyl, haloC$_{1-4}$alkoxy, cyano, nitro, amino, C$_{1-4}$alkylamino, aminoC$_{1-4}$alkyl, hydroxyC$_{1-4}$alkyl, C$_{1-4}$alkoxy, thiol, and/or C$_{1-4}$alkylthio. For the avoidance of doubt, a "substituted lower alkyl" means an alkyl group having one to four carbon atoms and one to four substituents selected from those recited immediately above for substituted alkyl groups. In the case of a substituted lower alkyl, preferably the groups R$_a$ and R$_b$ are selected from hydrogen, lower alkyl, lower alkenyl, C$_{3-7}$cycloalkyl, phenyl, and five to six membered monocyclic heterocyclo and/or heteroaryl, in turn optionally substituted as above.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include alkyl, substituted alkyl, and those groups recited above as alkyl substituents.

The terms "alkoxy" and "alkylthio" refer to an alkyl group as described above bonded through an oxygen linkage (—O—) or a sulfur linkage (—S—), respectively. The terms "substituted alkoxy" and "substituted alkylthio" refer to a substituted alkyl group as described above bonded through an oxygen or sulfur linkage, respectively. A "lower alkoxy" or a C$_{1-4}$alkoxy is a group OR, wherein R is lower alkyl (alkyl of 1 to 4 carbon atoms).

"Amino" is —NH$_2$. An alkylamino is —NR$_c$R$_d$ wherein at least one of R$_c$ and R$_d$ is an alkyl or substituted alkyl, and the other of R$_c$ and R$_d$ is selected from hydrogen, alkyl, and substituted alkyl. An "aminoalkyl" means an amino group bonded through an alkylene group (-alkylene-NH$_2$), and an alkylaminoalkyl means an alkylamino as defined above bonded through an alkylene group (-alkylene-NR$_c$R$_d$).

The term "aryl" refers to cyclic, aromatic hydrocarbon groups which have 1 to 3 aromatic rings, especially monocyclic or bicyclic groups such as phenyl or naphthyl. Aryl groups which are bicyclic or tricyclic must include at least one fully aromatic carbocyclic ring but the other fused ring or rings may be aromatic or non-aromatic and may optionally contain heteroatoms, provided that in such cases the point of attachment will be to the aromatic carbocyclic ring. Additionally, when an aryl group has fused thereto a heterocyclic or cycloalkyl ring, the heterocyclic and/or cycloalkyl ring may have one or more carbonyl groups, i.e., an oxygen atom attached via a double bond to define a carbonyl. Thus, examples of "aryl" may include without limitation:

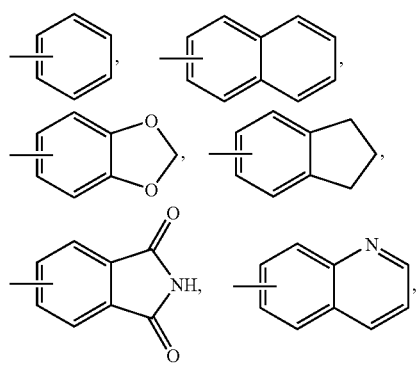

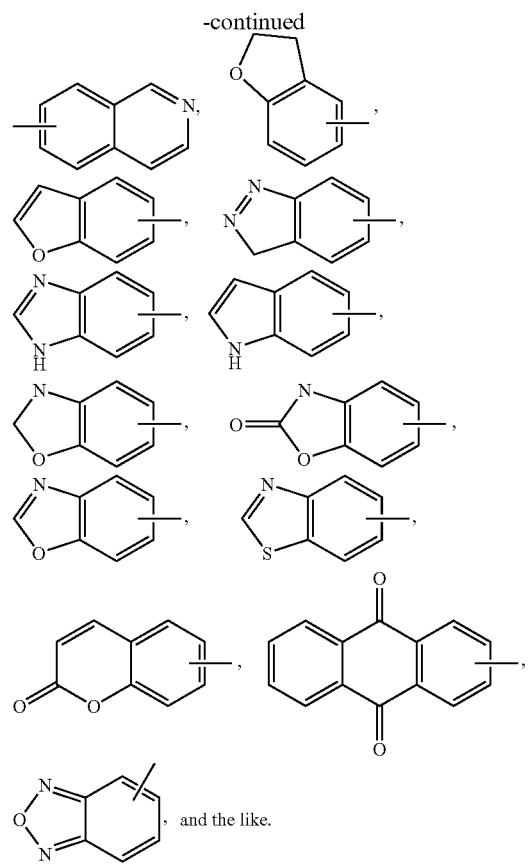

"Substituted aryl" refers to an aryl group as defined above substituted by one or more substituents, preferably 1 to 4 substituents, at any point of attachment. Substituents include alkyl, substituted alkyl, alkenyl, substituted alkenyl, as well as those groups recited above as alkyl substituents.

"Benzyl" is the group

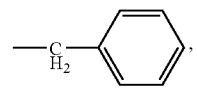

and "benzyloxy" is the group

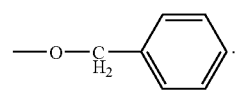

The term "carbocyclic" means a saturated or unsaturated monocyclic, bicyclic, or tricyclic ring (preferably mono- or bicyclic) in which all atoms of all rings are carbon. Thus, the term includes cycloalkyl and aryl rings which do not have heterocyclic groups fused thereto. The carbocyclic ring may be substituted in which case the substituents are selected from those recited herein for cycloalkyl and aryl groups.

The term "cycloalkyl" refers to a fully saturated or partially saturated cyclic hydrocarbon group containing from 1 to 3 rings and 3 to 7 carbon atoms per ring. Exemplary fully saturated cycloalkyl groups include cyclopropyl, cyclobutyl, cyclopentyl, and cyclohexyl. Exemplary partially saturated cycloalkyl groups include cyclobutenyl, cyclopentenyl, and cyclohexenyl. The term "cycloalkyl" includes such groups having a bridge including one or two bridge carbon atoms (such that the bridged ring will have three or four carbon atoms). Additionally, cycloalkyl groups which are bicyclic or tricyclic must include at least one fully saturated or partially saturated hydrocarbon ring but the other fused ring or rings may be aromatic or non-aromatic and may contain heteroatoms, provided that in such cases the point of attachment will be to the carbocyclic, non-aromatic ring. Additionally, one or more carbon atoms of the cycloalkyl group may form a carbon-to-oxygen double bond to define a carbonyl group. Thus, examples of "cycloalkyl" groups may include, without limitation:

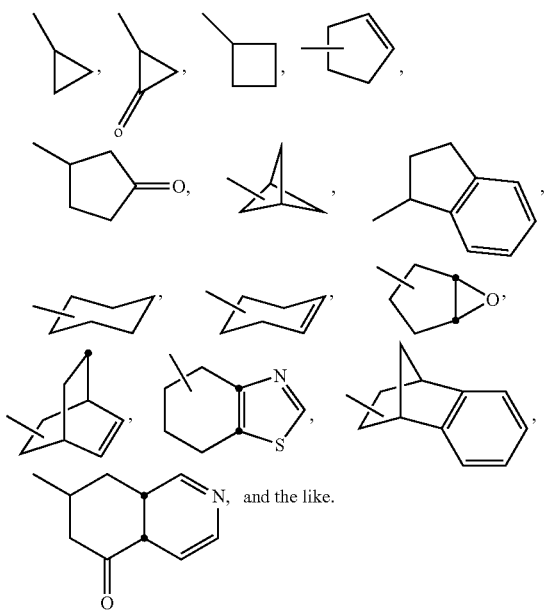

"Substituted cycloalkyl" refers to a cycloalkyl group as defined above substituted at any available point of attachment with one or more substituents, preferably 1 to 4 substituents. Cycloalkyl substituents include alkyl, substituted alkyl, alkenyl, substituted alkenyl, and those groups recited above as alkyl substituents.

The term "halogen" or "halo" refers to fluorine, chlorine, bromine and iodine (preferably F or Cl).

The term "heteroatoms" includes oxygen, sulfur and nitrogen.

The term "haloalkyl" means an alkyl (preferably lower alkyl) having one or more halo substituents, including without limitation groups such as —$CH_2F$, —$CHF_2$ and —$CF_3$.

The term "haloalkoxy" means an alkoxy group having one or more halo substituents. For example, "haloalkoxy" includes —$OCF_3$.

When the term "unsaturated" is used herein to refer to a ring or group, the ring or group may be fully unsaturated or partially unsaturated.

The term "heteroaryl" refers to an aromatic group which is a 4 to 7 membered monocyclic, 7 to 11 membered bicyclic, or 10 to 15 membered tricyclic ring system, which has at least one ring containing at least one heteroatom. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic and may be carbocyclic, provided that in such cases the point of attachment will be at any available nitrogen or carbon atom of an aromatic heteroatom-containing ring. Additionally, the definition of heteroaryl groups itself includes rings wherein one or more of the carbon atoms is attached via a double bond to an oxygen atom to define a carbonyl group (provided the heteroaryl group is aromatic) and also when a heteroaryl group has fused thereto a heterocyclic or cycloalkyl ring, the heterocyclic and/or cycloalkyl ring may have one or more carbonyl groups.

Exemplary monocyclic heteroaryl groups include pyrrolyl, pyrazolyl, pyrazolinyl, imidazolyl, oxazolyl, isoxazolyl, thiazolyl (i.e., 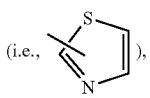), thiadiazolyl, isothiazolyl, furanyl, thienyl, oxadiazolyl, pyridyl, pyrazinyl, pyrimidinyl, pyridazinyl, triazinyl and the like. Additionally, since the definition of heteroaryl groups itself includes rings wherein one or more of the carbon atoms defines a carbonyl group, rings such as 2,4-dihydro-[1,2,4]triazol-3-one (i.e., 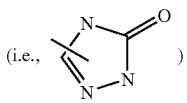)

and the like are included.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

"Substituted heteroaryl" groups are heteroaryl groups as defined above substituted with one or more substituents, preferably 1 to 4 substituents, at any available point of attachment. Exemplary substituents include, but are not limited to alkyl, substituted alkyl, alkenyl, substituted alkenyl, as well as those groups recited above as alkyl substituents.

The terms "heterocycle", heterocyclic" and "heterocyclo" are used interchangeably and each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. Heterocyclic groups which are bicyclic or tricyclic must include at least one non-aromatic non-carbocyclic ring, but the other fused ring or rings may be aromatic or non-aromatic and may be carbocyclic, provided that in such cases the point of attachment will be at any available nitrogen or carbon atom of a non-aromatic heteroatom-containing ring. Additionally, the definition of heterocyclic groups itself includes rings wherein one or more of the carbon atoms is attached via a double bond to an oxygen atom to define a carbonyl group (provided the heterocyclic group is non-aromatic) and also when a heterocyclic group has fused thereto a further ring, such further ring may have one or more carbonyl groups.

Exemplary monocyclic heterocyclic groups include pyrrolidinyl, imidazolidinyl, tetrahydrofuryl, piperidinyl, piperazinyl, pyrazolidinyl, imidazolinyl, pyrrolinyl, tetrahydropyranyl, morpholinyl, thiamorpholinyl, and the like.

"Substituted heterocycle," "substituted heterocyclic," and "substituted heterocyclo" refer to heterocycle, heterocyclic, or heterocyclo groups as defined above substituted with one or more substituents, preferably 1 to 4 substituents, at any available point of attachment. Exemplary substituents include alkyl, substituted alkyl, alkenyl, substituted alkenyl, as well as those groups recited above as exemplary alkyl substituents.

"Hydroxy" refers to —OH.

"Nitro" is —$NO_2$.

A "non-interfering substituent" is a substituent that may be attached to the hexahydroimidazo-pyrazin-3-one core of formula (I), applying synthetic techniques available to one skilled in the field and/or as described herein, and that does not substantially reduce the activity of the compound in modulating or binding to the androgen receptor (AR). By "substantially reduce" means that the activity of the compound in modulating the AR, and/or affinity of the compound in binding to the AR, is not reduced by more than a factor of 100 after the substituent is attached, as compared with when the substituent is not present. More preferred compounds having non-interfering substituents are those where there is less than a 50-fold reduction in activity, more preferably less than 10-fold reduction in activity, when the substituent is attached as compared with when it is not present. Thus, for example, if a compound is selected as demonstrating an $IC_{50}$ value of 1 nm in antagonizing the AR, e.g., using an assay as reported herein, a substituent is a non-interfering substituent if, when attached to that compound, the $IC_{50}$ value of the compound is 100 nm or less, more preferably 50 nm or less, and even more preferably 10 nm or less. However, a "non-interfering substituent" does not encompass a carbonyl oxygen atom attached to the ring via a double bond (i.e., the radical =O), at the $R_4/R_5$ position such as would form a hydantoin. For example, a "non-interfering substituent" may be selected from alkyl, substituted alkyl, or a substituent recited above for substituted alkyl groups. As a more preferred example, a "non-interfering substituent" may be selected from groups such as lower alkyl, substituted lower alkyl, halogen, cyano, haloalkyl, haloalkoxy, —$OR_a$, —$SR_a$, —C(=O)$R_a$, —C(=O)$OR_a$, —OC(=O)$R_a$, —OC(=O)$OR_a$, —$NR_aR_b$, —C(=O)$NR_aR_b$, —OC(=O)$NR_aR_b$, —S(=O)$R_a$, —S(O)$_2R_a$, —NHS(O)$_2R_a$, —NHS(O)$_2$NH$R_a$, —NHC(=O)NH$R_a$, —NHC(=O)$R_a$, —NHC(O)$_2R_a$, and —NHC(=N—CN)$R_a$, wherein $R_a$ and $R_b$ are independently selected from hydrogen, lower alkyl, and substituted lower alkyl. As a further preferred example, a "non-interfering substituent" may be selected from lower alkyl, hydroxy, amino, cyano, halogen, trifluoromethyl, and the like.

"Thiol" means the group —SH.

The term "quaternary nitrogen" refers to a tetravalent positively charged nitrogen atom including, for example, the positively charged nitrogen in a tetraalkylammonium group (e.g., tetramethylammonium or N-methylpyridinium), the positively charged nitrogen in protonated ammonium species (e.g., trimethylhydroammonium or N-hydropyridinium), the positively charged nitrogen in amine N-oxides (e.g., N-methyl-morpholine-N-oxide or pyridine-N-oxide), and the positively charged nitrogen in an N-amino-ammonium group (e.g., N-aminopyridinium).

When a functional group is termed "protected", this means that the group is in modified form to mitigate, especially preclude, undesired side reactions at the protected site. Suitable protecting groups for the methods and compounds described herein include, without limitation, those described in standard textbooks, including Greene, T. W. et al., *Protective Groups in Organic Synthesis*, Wiley, N.Y. (1991), incorporated herein by reference.

Unless otherwise indicated, any heteroatom depicted with unsatisfied valences is assumed to have hydrogen atoms sufficient to satisfy the valences.

Each reference to compounds of formula (I) herein is intended to include subformulae falling within or comprised by the scope of formula (I), e.g., formula (Ia), (Ib), (Ic), (I)*, (I)**, (Ia)* and (Ia)** etc, unless otherwise indicated. When it is stated that one (a first) compound or isomer is present "substantially free" of another (second) compound, this means there is less than 10%, more preferably less than 5%, and most preferably less than about 2 to 3% of the second compound present with the first compound.

In compounds of formula (I), the group L is recited to be read from left to right, and inserted into each respective formula in the manner in which it appears. Thus, for example, compounds of formula (I) wherein L is recited as -$A_1$-N($R_{10}$)C(=O)-$A_2$- means compounds having the formula,

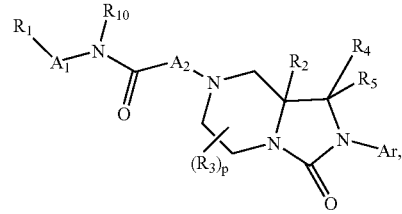

and compounds of formula (I) wherein L is recited as -$A_1$-C(=O)N$R_{10}$-$A_2$-, means compounds having the formula,

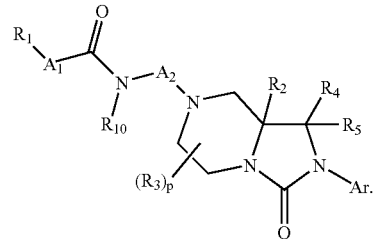

When reference is made herein to compounds that act as "antagonists" of the AR, this is intended to include compounds that act as full antagonists and/or partial antagonists, unless otherwise indicated.

The compounds of formula (I) may form salts which are also within the scope of this invention. Reference to a compound of the formula (I) herein is understood to include reference to salts thereof, unless otherwise indicated. The term "salt(s)", as employed herein, denotes acidic and/or basic salts formed with inorganic and/or organic acids and bases. In addition, when a compound of formula (I) contains both a basic moiety, such as but not limited to a pyridine or imidazole, and an acidic moiety such as but not limited to a carboxylic acid, zwitterions may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

The compounds of formula (I) that contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula (I) that contain an acidic moiety, such but not limited to a carboxylic acid, may form salts with a variety of organic and inorganic bases. Exemplary basic salts include ammonium salts; alkali metal salts such as sodium, lithium, and potassium salts; alkaline earth metal salts such as calcium and magnesium salts; salts with organic bases (for example, organic amines) such as benzathines, dicyclohexylamines, hydrabamines (formed with N,N-bis (dehydroabietyl)ethylenediamine), N-methyl-D-glucamines, N-methyl-D-glycamides, t-butyl amines; and salts with amino acids such as arginine, lysine, and the like. Basic nitrogen-containing groups may be quaternized with agents such as lower alkyl halides (e.g. methyl, ethyl, propyl, and butyl chlorides, bromides, and iodides), dialkyl sulfates (e.g. dimethyl, diethyl, dibutyl, and diamyl sulfates), long chain halides (e.g. decyl, lauryl, myristyl, and stearyl chlorides, bromides, and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula (I), or a salt and/or solvate thereof. Solvates of the compounds of formula (I) include, for example, hydrates.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. Racemic forms can be resolved by physical methods, such as, for example, fractional crystallization, separation or crystallization of diastereomeric derivatives, or separation by chiral column chromatography. Individual optical isomers can be obtained from stereospecific processes, wherein starting materials and/or intermediates are selected having a stereochemistry corresponding with that desired for the end products, and the stereochemistry is maintained throughout the reactions, and/or the isomers can be obtained from racemates by any suitable method, including without limitation, conventional methods, such as, for example, salt formation with an optically active acid followed by crystallization.

All configurational isomers of the compounds of the present invention are contemplated, either in admixture, or in pure or substantially pure form. As can be appreciated, the preferred configuration can be a function of the particular compound and the activity desired. Configurational isomers may be prepared by the processes described herein, which may be stereoselective. In other words, a desired stereochemistry for the final compounds can be achieved by using starting materials having the corresponding desired stereochemistry, and then maintaining the stereoselectivity throughout the process of preparation. Alternatively, the compounds may be prepared as racemates, and then the desired stereochemistry may be achieve via separation of configurational isomers which can be achieved by any suitable method known in the field, e.g., such as column chromatography.

Throughout the specifications, groups and substituents thereof may be chosen to provide stable moieties and compounds useful as pharmaceutically-acceptable compounds and/or intermediate compounds useful in making pharmaceutically-acceptable compounds. One skilled in the field will appreciate suitable selections for variables to achieve stable compounds.

Embodiments indicated herein as exemplary or preferred are intended to be illustrative and not limiting.

ALTERNATIVE EMBODIMENTS OF THE INVENTION

Various alternate aspects of the invention are contemplated. For example, according to one aspect of the invention, there are provided compounds having the formula (I),

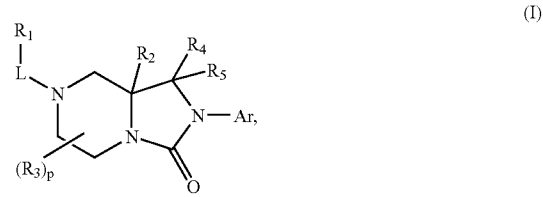

(I)

and/or pharmaceutically-acceptable salts thereof, wherein,

Ar is optionally-substituted phenyl or pyridyl (pyrid-2-yl, pyrid-3-yl or pyrid-4-yl);

L is -$A_1$-N(H)C(=O)-$A_2$-, -$A_1$-C(=O)NH-$A_2$-, -$A_1$-C(=O)-$A_2$-, -$A_1$-C(=O)O-$A_2$-, -$A_1$-OC(=O)-$A_2$-, -$A_1$-C(=$NR_{11}$)-$A_2$-, -$A_1$-C(=$NR_{11}$)NH-$A_2$-, -$A_1$-S-$A_2$-, -$A_1$-NH-$A_2$-, -$A_1$-S(O)$_2$-$A_2$-, -$A_1$-N(H)S(O)$_2$-$A_2$-, -$A_1$-S(O)$_2$N(H)-$A_2$-, or -$A_1$-$A_2$-;

$A_1$ is —(CH$_2$)$_m$—;

$A_2$ is —(CH$_2$)$_n$—;

$R_1$ is hydrogen, $C_{1-6}$alkyl, substituted $C_{1-6}$alkyl, aryl, substituted aryl, cycloalkyl, substituted cycloalkyl, heterocyclo, substituted heterocyclo, heteroaryl, or substituted heteroaryl, or when L is -$A_1$-$A_2$-, $R_1$ may also be cyano;

$R_2$ is hydrogen, lower alkyl, or substituted lower alkyl;

$R_3$ is at each occurrence individually selected from non-interfering substituents, and additionally two $R_3$ groups attached to the same carbon atom optionally may be taken together to form a carbonyl group;

$R_4$ and $R_5$ are individually selected from hydrogen and non-interfering substituents;

$R_{11}$ is hydrogen or cyano;

m and n are each independently 0 to 5; and p is 0 to 4;

with the proviso, however, that compounds having the formula,

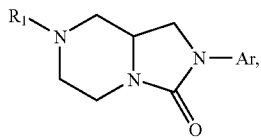

wherein $R_1$ is methyl or unsubstituted phenyl, Ar is

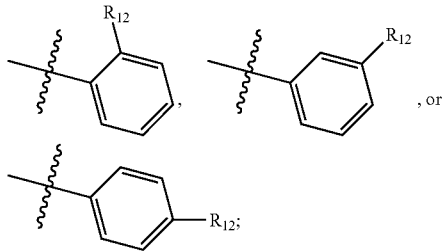

and $R_{12}$ is hydrogen, methyl, chloride, or methoxy; are excluded.

In compounds of formula (I), as recited above, the non-interfering substituents preferably may be selected from alkyl, substituted alkyl, or a substituent recited above for substituted alkyl groups; more preferably, from groups such as lower alkyl, substituted lower alkyl, halogen, cyano, haloalkyl, haloalkoxy, —$OR_{24}$, —$SR_{24}$, —C(=O)$R_{24}$, —C(=O)$OR_{24}$, —OC(=O)$R_{24}$, —OC(=O)$OR_{24}$, —$NR_{24}R_{25}$, —C(=O)$NR_{24}R_{25}$, —OC(=O)$NR_{24}R_{25}$, —S(=O)$R_{24}$, —S(O)$_2R_{24}$, —NHS(O)$_2R_{24}$, —NHS(O)$_2$NH$R_{24}$, —NHC(=O)NH$R_{24}$, —NHC(=O)$R_{24}$, —NHC(O)$_2$ $R_{24}$, and —NHC(=N—CN)$R_{24}$, wherein $R_{24}$ and $R_{25}$ are independently selected from hydrogen, lower alkyl, and substituted lower alkyl. According to another embodiment, the non-interfering substituents preferably are selected from lower alkyl, halogen, cyano, hydroxy, lower alkoxy, trifluoromethyl, trifluoromethoxy, amino, $C_{1-4}$alkylamino, amino$C_{1-4}$alkyl, —CO$_2$H, —CO$_2$(lower alkyl), —C(=O)H, —C(=O)(lower alkyl), —SO$_2$(lower alkyl), —SO$_2$(amino), and a $C_{1-4}$alkyl substituted with one to two of halogen, cyano, hydroxy, lower alkoxy, trifluoromethyl, trifluoromethoxy, amino, $C_{1-4}$alkylamino, amino$C_{1-4}$alkyl, —CO$_2$H, —CO$_2$(lower alkyl), —C(=O)H, —C(=O)(lower alkyl), —SO$_2$(lower alkyl), and/or —SO$_2$(amino).

In the interest of avoiding repetition, the proviso recited above, with regard to compounds of the invention (as opposed to methods of treatment or use) is intended to apply throughout the instant specification and claims, where applicable, and will not be restated with regard to each applicable alternative embodiment recited herein. See also, Omodei-Sale, A., and Toja, E., "Hexahydroimidazo[1,5-a]pyrazines" Farmaco, Edizione Scientifica (1975), Vol. 30(8), pp. 650-55, and Toja E., et al., "Hexahydroimidazo[1,5-a]pyrazines" Farmaco, Edizione Scientifica (1983), Vol. 39(5), pp. 450-462.

According to another embodiment, there are provided compounds having the stereochemistry as in formula (I)* and (I)**,

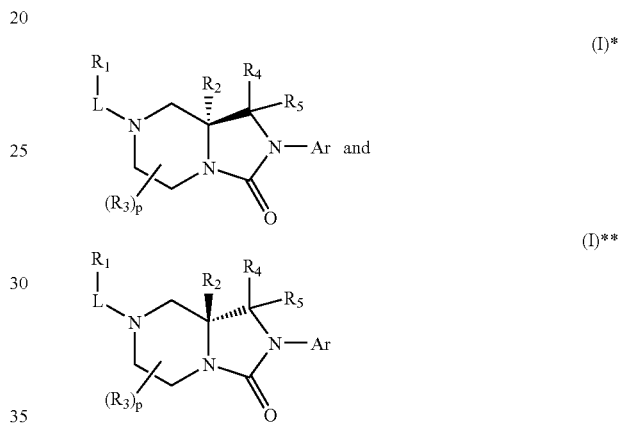

wherein each of the groups Ar, L, $R_1$, $R_2$, $R_3$, $R_4$, $R_5$ and p are as described above for a compound of formula (I), or as in the Summary of Invention, or otherwise as stated herein for alternative embodiments of the invention.

According to another embodiment, there are provided compounds of the formula (I)*, substantially free of compounds of the formula (I), and according to another embodiment, there are provided compounds of the formula (I), substantially free of compounds of the formula (I)*, wherein the variables Ar, L, $R_1$, $R_2$, $R_3$, $R_4$, $R_5$ and p are as defined immediately above, or as elsewhere described herein for alternative embodiments for compounds of formula (I). It should be understood that reference to compounds of formula (I), comprise compounds of formula (I)* and (I)**, unless otherwise indicated.

According to another embodiment, there are provided compounds according to formula (I), wherein p is 0 to 2, more preferably, wherein p is 0 (i.e., there is no substituent $R_3$). In such cases, the remaining substituents may be selected from those recited in the Summary of Invention, or as otherwise set forth herein with reference to alternative embodiments.

According to another embodiment, there are provided compounds according to formula (I), wherein $R_2$ is hydrogen, methyl, ethyl, isopropyl, or —(CH$_2$)$_v$($R_{20}$), wherein v is 1 or 2, and $R_{20}$ is hydroxy, methoxy, trifluoromethyl, or N-morpholinyl, and in another embodiment, $R_2$ may be hydrogen or methyl. In such cases, the remaining substituents may be selected from those recited in the Summary of Invention, or as otherwise set forth herein with reference to alternative embodiments.

According to another embodiment, there are provided compounds having the formula (Ia),

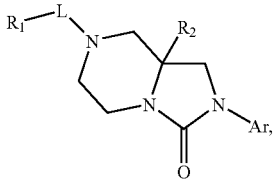

(Ia)

and/or pharmaceutically-acceptable salts thereof, wherein the groups Ar, $R_1$, $R_2$ and L are as defined herein for compounds of formula (I), e.g., as recited in the Summary of Invention, or as otherwise set forth herein with reference to alternative embodiments.

According to another embodiment of the invention, there are provided compounds according to the formula (Ia),

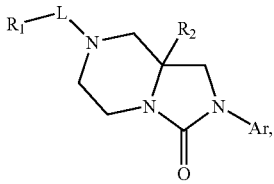

(Ia)

wherein,

Ar is aryl, substituted aryl, heteroaryl, or substituted heteroaryl wherein Ar is attached to the core ring via a carbon atom of Ar (more preferably Ar is optionally-substituted phenyl or pyridyl);

L is selected from $-A_1-N(H)C(=O)-A_2-$, $-A_1-C(=O)NH-A_2-$, $-A_1-C(=O)-A_2-$, $-A_1-C(=O)O-A_2-$, $-A_1-OC(=O)-A_2-$, $-A_1-C(=N-CN)-A_2-$, $-A_1-C(=N-CN)NH-A_2-$, $-A_1-S-A_2-$, $-A_1-NH-A_2-$, $-A_1-S(O)_2-A_2-$, $-A_1-NHS(O)_2-A_2-$, $-A_1-S(O)_2NH-A_2-$ and $-A_1-A_2-$;

$A_1$ is $-(CH_2)_m-$;

$A_2$ is $-(CH_2)_n-$;

$R_1$ is selected from aryl, substituted aryl, heteroaryl, and substituted heteroaryl (more preferably $R_1$ is optionally-substituted phenyl, pyridyl, or pyrimidinyl);

$R_2$ is hydrogen, methyl, ethyl, isopropyl, or $-(CH_2)_v$ ($R_{20}$);

$R_{20}$ is hydroxy, methoxy, trifluoromethyl, or N-morpholinyl;

m and n are each independently 0 to 5, more preferably 0 to 3; and v is 1 or 2.

According to another embodiment of the invention, there are provided compounds having the formula (Ia)* and/or (Ia)**,

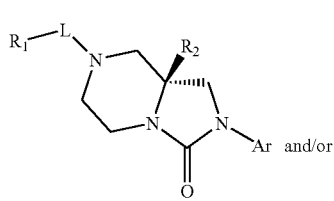

(Ia)* and/or

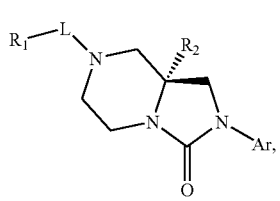

(Ia)**

wherein the variables Ar, L, $R_1$ and $R_2$ are as defined immediately above for compounds of formula (Ia), or as elsewhere described herein for alternative embodiments for compounds of formula (I) or (Ia).

According to another embodiment, there are provided compounds of the formula (Ia)*, substantially free of compounds of the formula (Ia), and according to another embodiment, there are provided compounds of the formula (Ia), substantially free of compounds of the formula (Ia)*, wherein the variables Ar, L, $R_1$ and $R_2$ are as defined above, or as elsewhere described herein for alternative embodiments for compounds of formula (Ia).

According to another embodiment, there are provided compounds according to either of formula (I) or (Ia), above, wherein the group $R_1$ is selected from hydrogen, cyano, $C_{1-6}$alkyl, substituted $C_{1-6}$alkyl (preferably wherein such substituents where valence allows are selected from cyano, and/or up to 7 halogen groups, preferably F), optionally-substituted $C_{3-7}$cycloalkyl (more preferably cyclopropyl or cyclohexyl), five or six membered heterocyclo (more preferably piperidinyl, piperazinyl, or N-morpholinyl), aryl (more preferably phenyl), and heteroaryl (more preferably thiazolyl, benzothiazolyl, pyridinyl, or pyrimidinyl), wherein each such cycloalkyl, heterocyclo, aryl or heteroaryl group in turn is optionally substituted with one to four groups as valence allows selected from halogen (preferably F or Cl), lower alkyl, haloalkyl (e.g., trifluoromethyl), methoxy, cyano, $SO_2$ (lower alkyl), and/or phenyl, wherein said phenyl again in turn is optionally substituted (preferably with one to three groups selected from lower alkyl, halogen, trifluoromethyl, cyano, trifluoromethoxy, and the like).

According to another embodiment, there are provided compounds according to formula (I) or (Ia), wherein the group L is selected from $-(CH_2)_r-$, $-S-(CH_2)_r-$, $-S(O)_2-$, $-OC(=O)-$, $-C(=O)(CH_2)-$, $-CH_2-O-C(=O)-$, $-(CH_2)_rN(H)C(=O)-$, $-NHS(O)_2-$, $-S(O)_2NH-$, and $-N(H)C(=NCN)-$, wherein r is 0 to 6. Preferably, when L is $-S-(CH_2)_r-$, r is 2; when L is $-C(=O)(CH_2)_r-$, preferably r is 0, 3, or 5; and when L is $-(CH_2)_rN(H)C(=O)-$, preferably r is 0, 1, or 4. According to another aspect of the invention, L is selected from a bond, $-N(H)C(=O)-$, and $-OC(=O)-$.

According to another embodiment, there are provided compounds according to formula (I) or (Ia), above, wherein the group Ar is

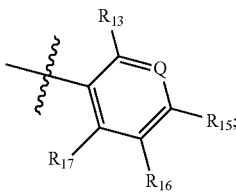

wherein Q is N or $CR_{14}$ and $R_{13}$, $R_{14}$, $R_{15}$, $R_{16}$, and $R_{17}$, are independently selected from hydrogen, lower alkyl, halogen, cyano, haloalkyl, haloalkoxy, lower alkoxy, and lower alkyl substituted with one to three of halogen, cyano, haloalkyl, haloalkoxy, and/or lower alkoxy.

According to another embodiment, there are provided compounds according to formula (I) or (Ia), above, wherein the group Ar is

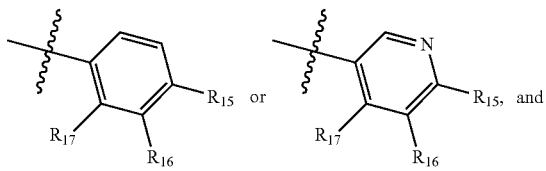

$R_{15}$, $R_{16}$ and $R_{17}$ are selected from hydrogen, halogen, methyl, cyano, methoxy, and trifluoromethyl ($R_{15}$ more preferably is cyano).

According to another embodiment of the invention, there are provided compounds having the formula (Ib),

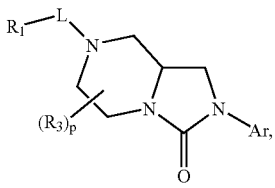

(Ib)

wherein,
the group Ar is

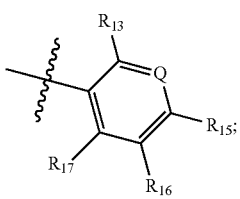

Q is N or $CR_{14}$;

L is selected from —$(CH_2)_r$—, —S—$(CH_2)_r$—, —S$(O)_2$—, —OC(=O)—, —C(=O)$(CH_2)_r$—, —$CH_2$—O—C(=O)—, —$(CH_2)_r$N(H)C(=C)—, —NHS$(O)_2$—, —S$(O)_2$NH—, and —N(H)C(=NCN), wherein r is 0 to 6;

$R_1$ is selected from hydrogen, cyano, $C_{1-6}$alkyl, substituted $C_{1-6}$alkyl (preferably wherein such substituents where valence allows are selected from cyano, and/or up to 7 halogen groups, preferably F), optionally-substituted $C_{3-7}$cycloalkyl (more preferably cyclopropyl or cyclohexyl), five or six membered heterocyclo (more preferably piperidinyl, piperazinyl, or N-morpholinyl), aryl (more preferably phenyl), and heteroaryl (more preferably thiazolyl, benzothiazolyl, pyridinyl, or pyrimidinyl), wherein each such cycloalkyl, heterocyclo, aryl or heteroaryl group in turn is optionally substituted with one to four groups as valence allows selected from halogen (preferably F or Cl), lower alkyl, haloalkyl (e.g., trifluoromethyl), methoxy, cyano, $SO_2$(lower alkyl), and/or phenyl, wherein said phenyl again in turn is optionally substituted (preferably with one to three groups selected from lower alkyl, halogen, trifluoromethyl, cyano, and trifluoromethoxy);

$R_3$ is at each occurrence independently selected from lower alkyl, halogen, cyano, hydroxy, lower alkoxy, trifluoromethyl, trifluoromethoxy, amino, $C_{1-4}$alkylamino, amino$C_{1-4}$alkyl, —$CO_2H$, —$CO_2$(lower alkyl), —C(=O)H, —C(=O)(lower alkyl), —$SO_2$(lower alkyl), —$SO_2$(amino), and a $C_{1-4}$alkyl substituted with one to two of halogen, cyano, hydroxy, lower alkoxy, trifluoromethyl, trifluoromethoxy, amino, $C_{1-4}$alkylamino, amino$C_{1-4}$alkyl, —$CO_2H$, —$CO_2$(lower alkyl), —C(=O)H, —C(=O)(lower alkyl), —$SO_2$(lower alkyl), and/or —$SO_2$(amino);

$R_{13}$, $R_{14}$, $R_{15}$, $R_{16}$, and $R_{17}$ are independently selected from hydrogen, lower alkyl, halogen, cyano, haloalkyl, haloalkoxy, lower alkoxy, and a lower alkyl substituted with one to two of halogen, cyano, haloalkyl, haloalkoxy, and/or lower alkoxy; and p is 0, 1 or 2.

According to another embodiment of the invention, there are provided compounds having the formula (Ic),

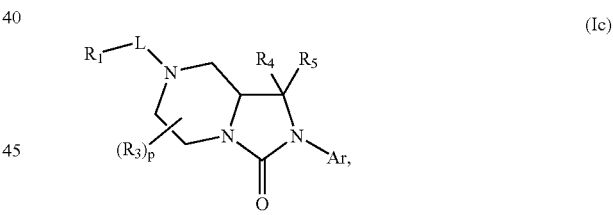

(Ic)

wherein the various groups are as selected above for compounds of formula (I), (Ia), and/or (Ib), more preferably, they are as recited immediately above for compounds of formula (Ib). In compounds of formula (Ic), preferably both $R_4$ and $R_5$ are selected from hydrogen, lower alkyl, halogen, cyano, hydroxy, lower alkoxy, trifluoromethyl, trifluoromethoxy, amino, $C_{1-4}$alkylamino, amino$C_{1-4}$alkyl, —$CO_2H$, —$CO_2$(lower alkyl), —C(=O)H, —C(=O)(lower alkyl), —$SO_2$(lower alkyl), —$SO_2$(amino), and a $C_{1-4}$alkyl substituted with one to two of halogen, cyano, hydroxy, lower alkoxy, trifluoromethyl, trifluoromethoxy, amino, $C_{1-4}$alkylamino, amino$C_{1-4}$alkyl, —$CO_2H$, —$CO_2$(lower alkyl), —C(=O)H, —C(=O)(lower alkyl), —$SO_2$(lower alkyl), and/or —$SO_2$(amino).

Also, the groups $R_1$-L- in each of the above formulae taken together may preferably be selected from:

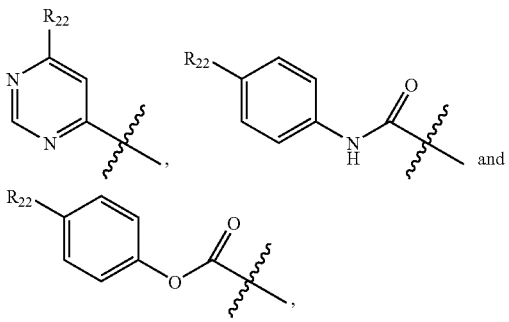

wherein R$_{22}$ is preferably halogen (more preferably F or Cl).

Also preferred are the compounds which are (S,E)-((2-(4-cyano-3-(trifluoromethyl)phenyl)-3-oxo-hexahydroimidazo[1,5-a]pyrazin-7(1H)-yl)(2-methoxyphenyl)methylene)cyanamide; (S)-2-(4-cyano-3-(trifluoromethyl)phenyl)-N-(4-fluorophenyl)-3-oxo-hexahydroimidazo[1,5-a]pyrazine-7(1H)-carboxamide; (S)—N-(4-fluorobenzyl)-2-(4-cyano-3-(trifluoromethyl)phenyl)-3-oxo-hexahydroimidazo[1,5-a]pyrazine-7(1H)-carboxamide; (S)-4-(7-(6-chloropyrimidin-4-yl)-3-oxo-tetrahydroimidazo[1,5-a]pyrazin-2(1H,3H,5H)-yl)-2-(trifluoromethyl)benzonitrile; (R)-benzyl 2-(4-cyano-3-(trifluoromethyl)phenyl)-8a-methyl-3-oxo-hexahydroimidazo[1,5-a]pyrazine-7(1H)-carboxylate; (R)-benzyl 2-(3-chloro-4-cyano-2-methylphenyl)-8a-methyl-3-oxo-hexahydroimidazo[1,5-a]pyrazine-7(1H)-carboxylate; (S)-2-(4-cyano-3-(trifluoromethyl)phenyl)-N-(4-fluorophenyl)-8a-methyl-3-oxo-hexahydroimidazo[1,5-a]pyrazine-7(1H)-carboxamide; (S)-4-(7-(6-chloropyrimidin-4-yl)-8a-methyl-3-oxo-tetrahydroimidazo[1,5-a]pyrazin-2(1H,3H,5H)-yl)-2-(trifluoromethyl)benzonitrile; (S)-4-(7-(4-fluorobenzyl)-3-oxo-tetrahydroimidazo[1,5-a]pyrazin-2(1H,3H,5H)-yl)-2-(trifluoromethyl)benzonitrile; (S)-2-chloro-3-methyl-4-(3-oxo-7-(3-trifluoromethyl-4-cyanophenyl)-tetrahydroimidazo[1,5-a]pyrazin-2(1H,3H,5H)-yl)benzonitrile; and (ii) pharmaceutically-acceptable salts thereof.

Utility

The compounds of the present invention may be useful for modulating the function of the androgen receptor, particularly as antagonists or partial antagonists of the androgen receptor (AR). Selective modulation of the AR relative to other receptors within the NHR family is preferred.

The present compounds thus may be useful in the treatment of AR-associated conditions. "AR-associated condition", as used herein, denotes a condition or disorder which can be treated by modulating the function of the AR in a subject, wherein the term "treat" or "treatment" comprises prevention, alleviation (to any degree, be it minor, partial, substantial or complete), or cure of the condition or disorder or any of its symptoms. Modulation may occur locally, for example, within certain tissues of the subject, or more extensively throughout a subject being treated for such a condition or disorder.

The compounds of the present invention may be useful for the treatment of a variety of conditions and disorders including, but not limited to, those described below.

The compounds of formula (I) may be used to treat one or more of the following conditions: hirsutism, acne, seborrhea, Alzheimer's disease, androgenic alopecia, hypogonadism, hyperpilosity, benign prostate hypertrophia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers, modulation of VCAM expression and applications therein for the treatment of heart disease, inflammation and immune modulations, modulation of VEGF expression and the applications therein for use as antiangiogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients. For example, pan AR modulation is contemplated, with prostate selective AR modulation ("SARM") being particularly preferred, such as for the treatment of early stage prostate cancers. In one embodiment, one or more compounds of this invention are employed as antagonists or partial antagonists to the androgen receptor in the treatment of prostate cancer.

The compounds of formula (I) can be applied as (preferably, selective) antagonists of the mutated androgen receptor, for example, found in many tumor lines. Examples of such mutants are those found in representative prostate tumor cell lines such as LNCap, (T877A mutation, *Biophys. Acta*, 187, 1052 (1990)), PCa2b, (L701H & T877A mutations, *J Urol.*, 162, 2192 (1999)) and CWR22, (H874Y mutation, *Mol. Endo.*, 11, 450 (1997)). Applications of said compounds include but are not limited to: adenomas and neoplasies of the prostate, breast cancer, and endometrial cancer.

The present invention also provides pharmaceutical compositions comprising at least one of the compounds of the formula (I), and a pharmaceutically-acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention may be useful in treating any of the conditions or disorders listed or described herein such as cancers or other proliferate diseases, and in compositions for treating such conditions or disorders, without limitation as to their mechanism of action. The present invention also provides methods of treating subjects, preferably mammals such as humans, for disorders or conditions associated with the function of the AR.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol™ 934 polymer, B.F. Goodrich Co., NY). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of the compound of the present invention can be determined by one of ordinary skill in the art, and includes exemplary dosage amounts for an adult human of from about 1 to 250 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include mammalian species such as humans, and domestic animals such as dogs, cats and the like, subject to AR-associated conditions. Treatment of humans is preferred.

The compounds of the present invention can be employed alone or in combination with each other and/or other suitable therapeutic agents useful in the treatment of AR-associated conditions such as cancer, particularly, prostate cancer. In treating cancer, a combination of compounds of the instant invention and one or more additional agents and/or other treatments may be advantageous. The second agent may have the same or different mechanism of action than the compounds of formula (I).

Examples of classes of such other agents useful in combination with the present compounds may include one or more agents selected from: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as tamoxifen, glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and analogs thereof, and epothilones A-F and analogs thereof, for example, the aza-epothilone B analog known as ixabepilone; plant-derived products, such as vinca alkaloids, epipodophyllotoxins; topiosomerase inhibitors such as CPT-11 or topotecan; prenyl-protein transferase inhibitors; platinum coordination complexes such as cisplatin and carboplatin; thymidilate synthase inhibitors; antiangiogenic agents, such as matrix metalloproteinase inhibitors and VEGF inhibitors (e.g., ZD6474, ZD6126 and comberstatin A2); kinase inhibitors, such as her2 specific antibodies, Iressa and CDK inhibitors; histone deacetylase inhibitors, such as CI-994 and MS-27-275; miscellaneous agents such as hydroxyurea, procarbazine, mitotane, hexamethylmelamine; and other agents used as anti-cancer and cytotoxic agents such as biological response modifiers, growth factors; immune modulators and monoclonal antibodies.

The anti-cancer agent(s) used in combination with compounds of the instant invention may be small molecules and/or antibodies. Anti-Her2 antibodies from Genentech may be used (e.g., HERCEPTIN™ or trastuzumab). A suitable EGFR inhibitor is EKB-569 (an irreversible inhibitor). Also included are Imclone antibody C225 immunospecific for the EGFR (i.e., Erbitux). In one aspect, a compound of the invention is administered in combination with a CTLA-4 antibody. A further application is in concert with vaccine/immune modulating agents for the treatment of cancer.

The compounds of the invention may also be used in conjunction with other anti-cancer treatments such as surgery and/or radiation therapy.

Compounds of the invention used in combination with such other anti-cancer agents may produce a greater therapeutic advantage than obtainable via administration of a single dosage unit of compounds of the invention, and/or single dosage unit of such other anti-cancer agents, when administered alone. Synergistic or better than additive efficacious results or other improved advantages may be achieved, e.g., in terms of efficacy, safety, ease of administration, duration of administration, dosing, and the like.

Representative examples of other anti-cancer and/or cytotoxic agents that may be used in combination with compounds of the invention include but are not limited to mechlorethamine hydrochloride, carminomycin, cyclophosphamide, chlorambucil, melphalan, ifosfamide, busulfan, carmustin, lomustine, semustine, streptozocin, thiotepa, dacarbazine, methotrexate, methopterin, mitomycin C, thioguanine, mercaptopurine (e.g., 6-mercaptopurine), fludarabine, pentastatin, cladribin, cytarabine, fluorouracil (5-fluorouracil), capecitabine, doxorubicin hydrochloride, daunorubicin, idarubicin, bleomycin sulfate, actinomycin D, safracins, saframycins, quinocarcins, discodermolides, vincristine, vinblastine, vinorelbine tartrate, paclitaxel, tamoxifen, estramustine, estramustine phosphate sodium, flutamide, bicalutamide, nilutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine, altretamine, topoteca, Herceptin®, Erbitux, cisplatin, carboplatin, aminopterin, ecteinascidin 743, porfiromycin, cytosine arabinoside, podophyllotoxin or podophyllotoxin derivatives such as etoposide, etoposide phosphate or teniposide, melphalan, leurosidine, vindesine, leurosine, and any analogs or derivatives thereof.

Further examples of anticancer agents that may be used in combination with the compounds of the invention include inhibitors of Src Kinase, such as 'N-(2-Chloro-6-methylphenyl)-2-[[6-[4-(2-hydroxyethyl)-1-piperazinyl]-2-methyl-4-pyrimidinyl]amino]-5-thiazolecarboxamide, and other compounds described in U.S. Pat. No. 6,596,746 and U.S. patent application Ser. No. 11/051,208, filed Feb. 4, 2005, incorporated herein by reference; ixabepilone, an aza-epothilone B analog, and/or other epothilone analogs described in U.S. Pat. No. 6,605,599, U.S. Pat. No. 6,262,094, U.S. Pat. No. 6,288,237, U.S. Pat. No. 6,291,684, U.S. Pat. No. 6,359,140, U.S. Pat. No. 6,365,749, U.S. Pat. No. 6,380,395, U.S. Pat. No. 6,399,638, U.S. Pat. No. 6,498,257, U.S. Pat. No. 6,518,421, U.S. Pat. No. 6,576,651, U.S. Pat. No. 6,593,115, U.S. Pat. No. 6,613,912, U.S. Pat. No. 6,624,310, German Patent No. 4138042.8; WO 97/19086, WO 98/22461, WO 98/25929, WO 98/38192, WO 99/01124, WO 99/02514, WO 99/03848, WO 99/07692, WO 99/27890, WO 99/43653, WO 99/54330, WO 99/54318, WO 99/54319, WO 99/67252, WO 00/00485, WO 03/022844, US2004/0053910 and US2004/0152708; cyclin dependent kinase inhibitors found in WO 99/24416 (see also U.S. Pat. No. 6,040,321); prenyl-protein transferase inhibitors found in WO 97/30992 and WO 98/54966; farnesyl protein transferase agents such as those described in U.S. Pat. No. 6,011,029; CTLA-4 antibodies described in PCT publication no. WO01/14424 such as, for example, the antibody known as MDX-010, and/or a CTLA-4 antibody described in PCT publication no. WO00/37504 such as, for example, the antibody known as CP-675206.

The compounds of the present invention can also be formulated or co-administered with other therapeutic agents that are selected for their particular usefulness in administering therapies associated with the aforementioned conditions. For example, compounds of the invention may be formulated with agents to prevent nausea, hypersensitivity and gastric irritation, such as antiemetics, and $H_1$ and $H_2$ antihistaminics.

Such compounds may also be combined with agents which suppress the production of circulating testosterone such as LHRH agonists, antagonists, or with surgical castration.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists. The compounds of the present invention can be employed as AR antagonists in complete ablation therapy, alone or in combination with other AR antagonists such as Flutamide, Casodex, Nilutamide, and/or Cyproterone acetate.

The compounds of the present invention may be employed adjuvant to surgery.

The above other therapeutic agents, when employed in combination with the compounds of the present invention, can be used, for example, in those amounts indicated in the Physicians' Desk Reference (PDR) or as otherwise determined by one of ordinary skill in the art.

Compounds of the present invention, such as a number of exemplified compounds described herein, have been tested in one or more of the assays described below and/or assays known in the field, and demonstrate a measurable level of activity as having affinity for (e.g., binding to) the androgen receptor, and/or as modulators (e.g., antagonists) of the androgen receptor.

Transactivation Assays

MDA-MB-453 Androgen Receptor Transactivation Assay

The compounds of the recent invention can be tested in a cell based transactivation assay used to measure the antagonism of androgen receptor (AR) transcriptional activity. The transactivation assay provides a means of identifying antagonists that inhibit the effects of the native hormone dihydrotestosterone (DHT). The human breast adenocarcinoma MDA-MB-453 cell line (American Type Culture Collection, Rockville, Md., ATCC#: HTB-131), expressing a functional endogenous wild type AR, was transiently transfected with a reporter plasmid and tested for AR dependent transactivation activity in the absence or presence of test compounds. The pGL3 PSA-Luc reporter plasmid is comprised of the cDNA for the firefly luciferase gene and the upstream promoter sequences containing the androgen response elements (AREs) of the prostate specific antigen (PSA). This plasmid functions as a reporter for the transcription- modulating activity of the AR. In order to detect antagonists, the transactivation assay is conducted in the presence of constant concentration of the natural AR hormone (DHT) to induce a defined reporter signal. Addition of increasing concentrations of the suspected antagonist will decrease the reporter signal (luciferase activity).

MDA-MB-453 cells, maintained in DMEM (Cellgro, Cat. # 10-014-CM) supplemented with 10% FBS (Invitrogen/GIBCO Life Science), were seeded in a 96-well plate at 60,000 cells per well the evening prior to experimentation and incubated at 37° C. with 5% $CO_2$ until time of assay. Cell culture media from the 96-well cell plate was carefully removed by aspiration and each well was transfected with 100 ng pGL3 PSA-Luc plasmid by using the Lipofectamine 2000 Reagent (Invitrogen, Cat. # 11668-019) and serum-free Opti-MEM I media (Invitrogen, Cat# 31985-070) according to the manufacturer's optimized conditions. The transfection was conducted at 37° C. with 5% $CO_2$ for 4 hours.

Following the four hour transfection, DMEM containing 10% Charcoal/Dextran Treated Fetal Bovine Serum (Hyclone, Cat.# SH30068.03) was added to the cell plate. The cells were then incubated in the absence (blank) or presence (control) of 1 nM DHT (Sigma, Cat. # A-8380) and in the presence or absence of the standard antiandrogen bicalutamide or compounds in the present invention, in concentrations ranging from $10^{-10}$ to $10^{-5}$ M. Duplicates were used for each sample. The compound dilutions were performed by the Tecan Genesis (Tecan, Triangle Park, N.C.). After a 48 hour incubation, luciferase activity was measured using the Steady-Glo Luciferase Assay System (Promega, Cat. # E2550) according to manufacturer's specifications and luminescence was measured on a Packard TopCount (PerkinElmer). For each luciferase sample reading, the percent control (in absence of compounds) was calculated as:

% Control=100×[average sample−average blank]/
[average control-average blank]

Data was plotted and the $IC_{50}$ value was defined as the concentration of compound that inhibited 50% of the luciferase activity for the controls.

AR Binding Assay

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, are incubated at 37° C. to remove any endogenous ligand that might be complexed with the receptor in the cells. After 48 hours, either a saturation analysis to determine the K for tritiated dihydrotestosterone, [$^3$H]-DHT, or a competitive binding assay to evaluate the ability of test compounds to compete with [$^3$H]-DHT is performed. For the saturation analysis, media (RPMI 1640 or DMEM—0.2% CA-FBS) containing [$^3$H]-DHT (in concentrations ranging from 0.1 nM to 16 nM) in the absence (total binding) or presence (non-specific binding) of a 500-fold molar excess of unlabeled DHT are added to the cells. After 4 hours at 37° C., an aliquot of the total binding media at each concentration of [$^3$H]-DHT is removed to estimate the amount of free [$^3$H]-DHT. The remaining media is removed, cells are washed three times with PBS and harvested onto UniFilter GF/B plates (Packard), Microscint (Packard) is added and plates counted in a Top-Counter (Packard) to evaluate the amount of bound [$^3$H]-DHT.

For the saturation analysis, the difference between the total binding and the non-specific binding, is defined as specific binding. The specific binding is evaluated by Scatchard analysis to determine the $K_d$ for [$^3$H]-DHT. See e.g. D. Rodbard, *Mathematics and Statistics of Ligand Assays: An Illustrated Guide*: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M are added to the cells. Two replicates are used for each sample. After 4 hours at 37° C., cells are washed, harvested, and counted as described above. The data is plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand is quantified ($IC_{50}$) after log-logit transformation. The $K_1$ values are determined by application of the Cheng-Prusoff equation to the $IC_{50}$ values, where:

$$K_I = \frac{IC_{50}}{(1+(^3H\text{-}DHT)/K_d \text{ for } ^3H\text{-}DHT)}.$$

After correcting for non-specific binding, $IC_{50}$ values are determined. The $IC_{50}$ is defined as the concentration of competing ligand needed to reduce specific binding by 50%. The $K_d$ values for [$^3$H]-DHT for MDA 453 and LNCaP are 0.7 and 0.2 nM respectively.

Proliferation Assays

Murine Breast Cell Proliferation Assay

The ability of the compounds of the present invention to modulate the function of the AR can be determined by testing said compounds in a proliferation assay using the androgen responsive murine breast cell line derived from the Shionogi tumor, Hiraoka et al., *Cancer Res.*, 47, 6560-6564 (1987). Stable AR dependent clones of the parental Shionogi line are established by passing tumor fragments under the general procedures originally described in Tetuo, et. al., *Cancer Res.*, 25, 1168-1175 (1965). From the above procedure, one stable line, SC114, is isolated, characterized, and utilized for the testing of example compounds. SC114 cells are incubated with or without the test compounds for 72 hours and the amount of [$^3$H]-thymidine incorporated into DNA is quantified as a surrogate endpoint to assess the number of cells and therefore the proliferation rate as described in Suzuki et. al., *J. Steroid Biochem. Mol. Biol.* 37, 559-567 (1990). The SC114 cell line is maintained in MEM containing $10^{-8}$ M testosterone and 2% DCC-treated FCS. For the assay, cells are plated in 96-well microplates in the maintenance media and incubated at 37° C. On the following day, the medium is changed to serum free medium [Ham's F-12:MEM (1;1, v/v) containing 0.11% BSA] with (antagonist mode) or without (agonist mode) $10^8$ M testosterone and the test compounds of the present invention in concentrations ranging from $10^{-10}$ to $10^{-5}$ M. Duplicates are used for each sample. The compound dilutions are performed on a Biomek 2000 laboratory work station. Seventy two hours later 0.44 μCi of [$^3$H]-Thymidine (Amersham) is added per well and incubated for another 2 hr followed by tripsinization, and harvesting of the cells onto GF/B filters. Micro-scint PS is added to the filters before counting them on a Beckman TopCount.

For the antagonist mode, the % Inhibition is calculated as:

% Inhibition=100×(1−[(average$_{sample}$−average$_{blank}$)/
(average$_{control}$−average$_{blank}$)])

Data is plotted and the concentration of compound that inhibited 50% of the [$^3$H]-Thymidine incorporation is quantified ($IC_{50}$).

For the agonist mode % Control is referred as the effect of the tested compound compared to the maximal effect observed with the natural hormone, in this case DHT, and is calculated as:

% Control=100×(average$_{sample}$−average$_{blank}$)/(average$_{control}$−average$_{blank}$)

Data is plotted and the concentration of compound that inhibited 50% of the [$^3$H]-Thymidine incorporation is quantified ($EC_{50}$).

Wet Prostate Weight Assay AR Antagonist Assay:

The activity of compounds of the present invention as AR antagonists can be investigated in an immature male rat model, a standard, recognized test of antiandrogen activity of a given compound, as described in L. G. Hershberger et al., *Proc. Soc. Expt. Biol. Med.,* 83, 175 (1953); P. C. Walsh and R. F. Gittes, "Inhibition of extratesticular stimuli to prostate growth in the castrated rat by anti androgens", *Endocrinology,* 86, 624 (1970); and B. J. Furr et al., "ICI 176,334: A novel non-steroid, peripherally selective antiandrogen", *J. Endocrinol.,* 113, R7-9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. *Clin. Invest. Med.,* 16, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "*The Physiology of Reproduction*" ed. by E. Knobil and J. N. Deill, 1, 1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawely) are castrated under metofane anesthesia. Five days after surgery these castrated rats (60-70 g, 23-25 day-old) are dosed for 3 days. Animals are dosed subcutaneously (s.c.) 1 mg/kg with Testosterone Proprionate (TP) in arachis oil vehicle and anti-androgen test compounds (compounds of the present invention) are dosed orally by gavage (p.o.) in dissolved/suspensions of 80% PEG 400 and 20% Tween 80 surfactant(PEGTW). Animals are dosed (v/w) at 0.5 ml of vehicle/100 g body weight. Experimental groups are as follows:
1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") is administered (p.o. in PEGTW, QD) with TP (s.c. as administered in group 2) in a range of doses.
5. To demonstrate agonist activity a compound of the present invention ("test compound") is administered alone (p.o. in PEGTW, QD) in a range of doses.

At the end of the 3-day treatment, the animals are sacrificed, and the ventral prostate weighed. To compare data from different experiments, the sexual organs weights are first standardized as mg per 100 g of body weight, and the increase in organ weight induced by TP was considered as the maximum increase (100%). ANOVA followed by one-tailed Student or Fischer's exact test is used for statistical analysis.

The gain and loss of sexual organ weight reflect the changes of the cell number (DNA content) and cell mass (protein content), depending upon the serum androgen concentration. See Y. Okuda et al., *J Urol.,* 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight is 4 to 5-fold when dosing 3 mg/rat/day of testosterone (T) or 1 mg/rat/day of testosterone propionate (TP) for 3 days. The $EC_{50}$ of T and TP are about 1 mg and 0.03 mg, respectively. The increase in the weight of the VP and SV also correlates with the increase in the serum T and DHT concentration. Although administration of T shows 5-times higher serum concentrations of T and DHT at 2 hours after subcutaneous injection than that of TP, thereafter, these high levels decline very rapidly. In contrast, the serum concentrations of T and DHT in TP-treated animals are fairly consistent during the 24 hours, and therefore, TP showed about 10-30-fold higher potency than free T.

In this immature castrated rat model, a known AR antagonist (Casodex) is also administered simultaneously with 0.1 mg of TP ($ED_{80}$), inhibiting the testosterone-mediated increase in the weights of the VP and SV in a dose dependent manner. The antagonist effects are similar when dosing orally or subcutaneously. Compounds of the invention also exhibit AR antagonist activity by suppressing the testosterone-mediated increase in the weights of VP and SV.

CWR22 Human Prostate Zenograft Assay

In Vivo Antitumor Testing: CWR22 human prostate tumors are maintained in Balb/c nu/nu nude mice. Tumors are propagated as subcutaneous transplants in adult male nude mice (4-6 weeks old) using tumor fragments obtained from donor mice. Tumor passage occurs every 5-6 weeks.

For antitumor efficacy trial, the required number of animals needed to detect a meaningful response are pooled at the start of the experiment and each is given a subcutaneous implant of a tumor fragment (~50 mg) with a 13-gauge trocar. Tumors are allowed to grow to approx. 100-200 mg (tumors outside the range were excluded) and animals are evenly distributed to various treatment and control groups. Treatment of each animal is based on individual body weight. Treated animals are checked daily for treatment related toxicity/mortality. Each group of animals is weighed before the initiation of treatment ($Wt_1$) and then again following the last treatment dose ($Wt_2$). The difference in body weight ($Wt_2-Wt_1$) provides a measure of treatment-related toxicity.

Tumor response is determined by measurement of tumors with a caliper twice a week, until the tumors reach a predetermined "target" size of 0.5 gm. Tumor weights (mg) are estimated from the formula: Tumor weight=(length×width$^2$)÷2.

Tumor response end-point is expressed in terms of tumor growth inhibition (% T/C), defined as the ratio of median tumor weights of the treated tumors (T) to that of the control group (C).

To estimate tumor cell kill, the tumor volume doubling time is first calculated with the formula:

TVDT=[(Median time (days) for control tumors to reach target size)−(Median time (days) for control tumors to reach half the target size)].

And, Log cell kill=(T−C)÷(3.32×TVDT)

Statistical evaluations of data are performed using Gehan's generalized Wilcoxontest.

ABBREVIATIONS

The following abbreviations are used in the schemes and Examples herein for ease of reference:

Bop reagent=(benzotriazol-1-yloxy)tris(dimethylamino)phosphoniumhexafluorophosphate
CBZ-OSu=N-(Benzyloxycarbonyloxy)succinimide
DCM=dichloromethane
DEA=diethylamine
DIAD=diisopropyl azodicarboxylate
DIPEA=diisopropylethylamine
DMA=dimethylacetamide
EDC=1-(3-dimethylaminopropyl)-3-ethylcarbodiimide hydrochloride
EtOH=ethanol
EtOAc=ethyl acetate
iPr—OH or IPA=isopropyl alcohol
LDA=lithium diisopropylamide
MeI=methyl iodide
MeOH=methanol
Ph=phenyl
Pd/C=palladium on carbon
RT=room temperature
Sat'd=saturated
THF=tetrahydrofuran

Methods of Preparation

Compounds of formula (I) may generally be prepared according to the following schemes and the knowledge of one skilled in the art, and/or using methods set forth in the Examples that follow. In the schemes, the groups $R_1$, $R_2$, $R_3$, $R_4$, $R_5$, L, Ar, and p are as described herein for compounds of formula (I), unless otherwise indicated, and the term "PG" means protecting group as previously defined.

SCHEME 1

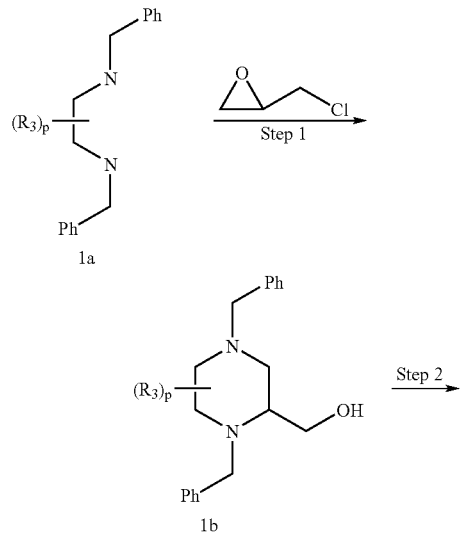

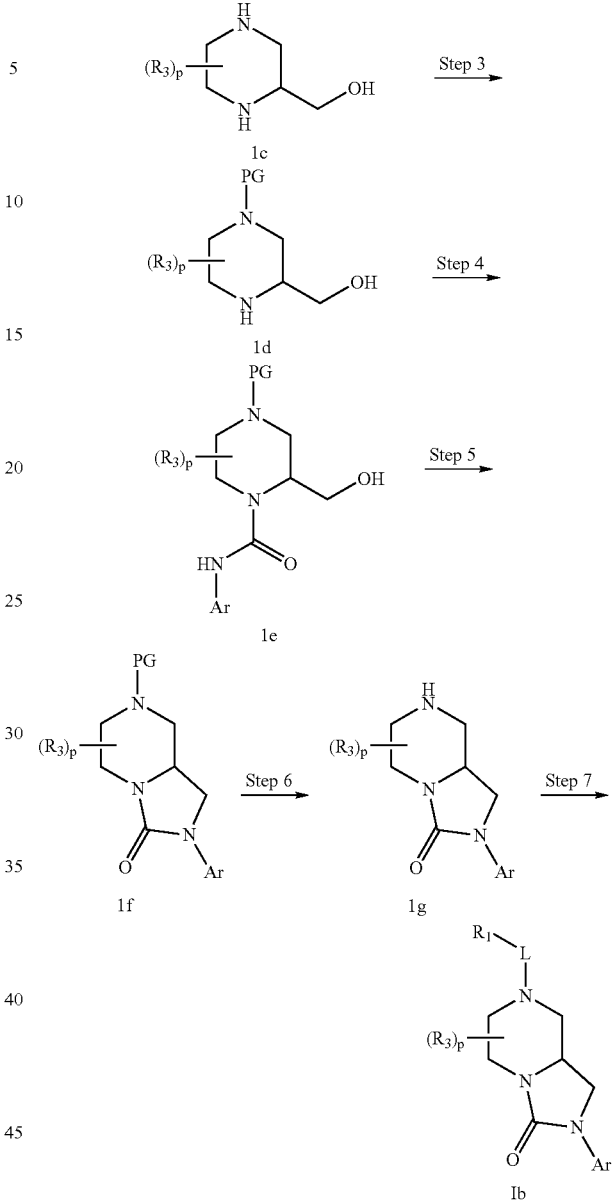

Compounds of formula (I) where $R_2$, $R_4$ and $R_5$=H, can be prepared as shown in Scheme 1, from compound 1a, which is commercially available or can be readily prepared by known methods such as reported by Basso, A. et al *J. Org. Chem.* 2005, 70, 575-579. In this report, $R_3$ is present in addition to a carbonyl group on the ethylene portion of the diamine. The carbonyl can be reduced to the unsubstituted methylene group without effecting $R_3$ by treatment with various reductants such as LAH or others known to one skilled in the art. For example, compounds 1b can be prepared by reacting N,N-dibenzylethylenediamine 1a in solvent such as EtOH with commercially available and enantiomerically pure epichlorohydrin. Compound 1b can be debenzylated by treatment under various conditions such as palladium on carbon in an atmosphere of hydrogen to give the piperazine 1c. Monoprotection of 1c can be accomplished by several methods known to one skilled in the art such as treatment with N-(benzyloxycarbonyloxy)succinimide in the presence of an amine base, to give an intermediate 1d. Compound 1d can be treated with N-aryl isocyanates or N-aryl-phenylcarbamates to afford a urea of formula 1e. Compound 1e can be treated under various conditions to give a cyclic urea of formula 1f. Such conditions could be p-toluenesulfonyl chloride in the presence of a base such as potassium tert-butoxide or standard conditions for a Mitsunobu reaction known to one skilled in the art. The protecting group in 1f can then be removed by treatment under acidic, basic or catalytic hydrogenation conditions depending on the nature of the protecting group to afford compound 1g. Compound 1g can be N-functionalized by numerous methods known to one skilled in the art to afford a compound of formula (Ib), a compound of formula (I).

2b as a mixture of diastereomers. A compound of formula (Ic) wherein $R_4$ and/or $R_5 \approx H$ can then be obtained from 2b by the steps outlined in Scheme 1.

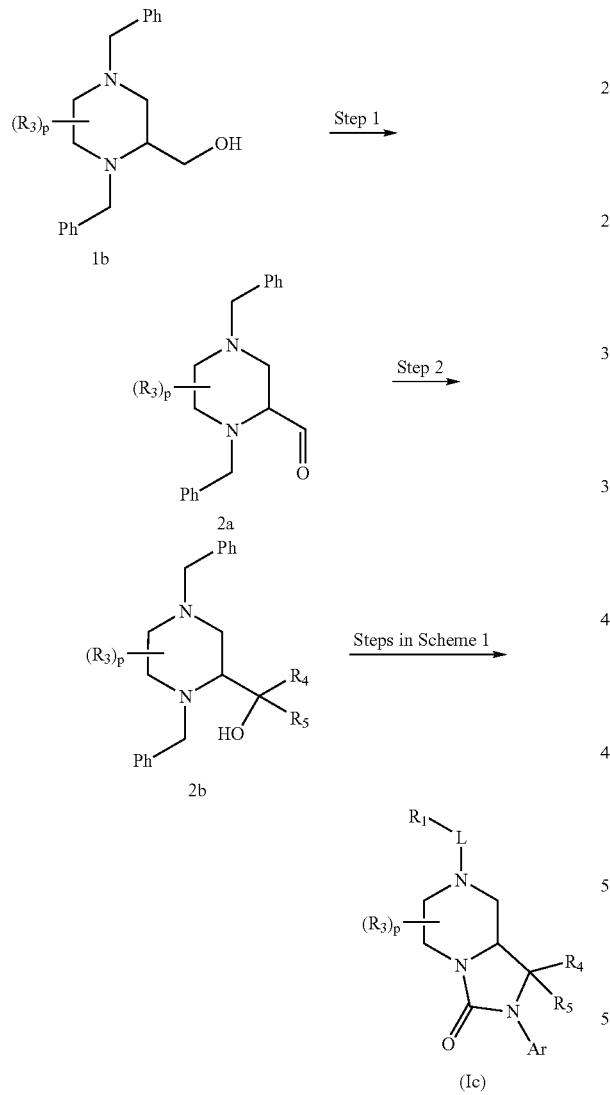

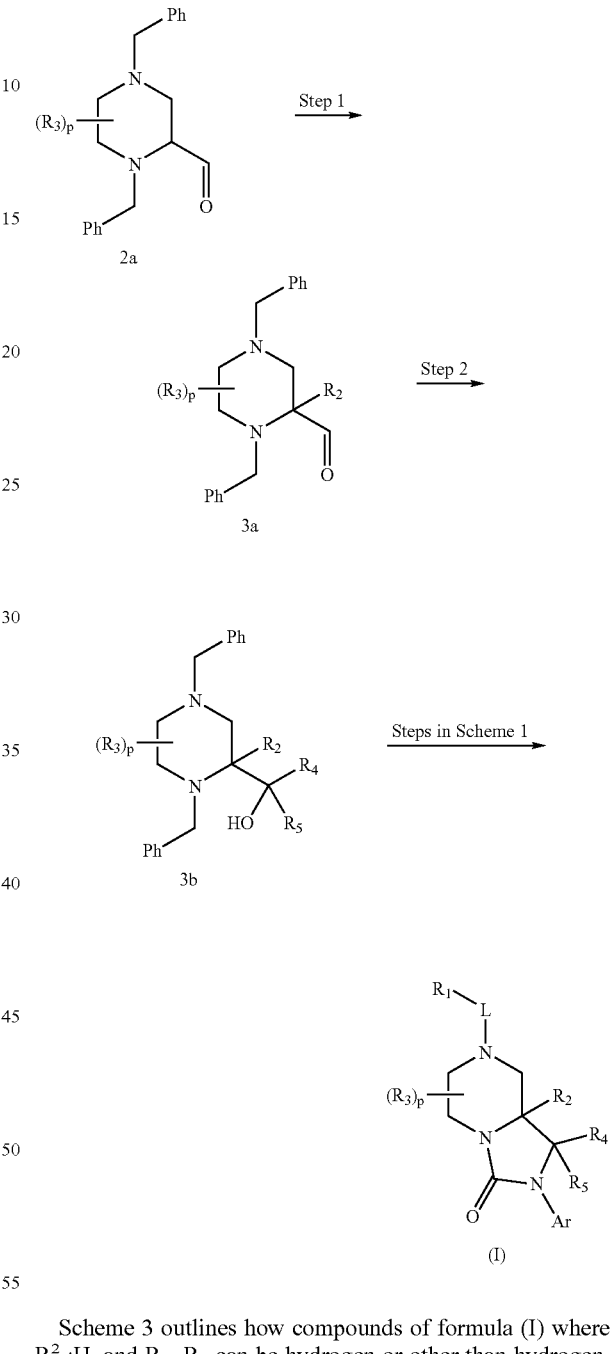

Scheme 2 depicts how compounds of formula (I) where $R_4$ and/or $R_5 \neq H$ can be prepared. Beginning with compound 1b oxidation of the primary alcohol to the corresponding aldehyde 2a can be accomplished by methods known to one skilled in the art such as Dess-Martin periodinane. Various organometallics, either readily prepared by one skilled in the art or commercially available (such as ethylmagnesium bromide) can be reacted with the aldehyde to afford compound Scheme 3 outlines how compounds of formula (I) where $R^2 \neq H$, and $R_4$, $R_5$ can be hydrogen or other than hydrogen, can be prepared from compound 2a. The aldehyde 2a can be treated with a base such as lithium diisopropylmine to generate the enolate followed by an electrophile such as methyliodide, to generate compound 3a as a mixture of enantiomers which can be separated by one skilled in the art. Compound 3a can then be reduced to the primary alcohol to yield compounds 3b, wherein $R_4$, $R_5 = H$, or can be treated with an organometallic as in Scheme 2 (such as ethyl magnesium bromide) to afford compound 3b, wherein $R_4$, $R_5 \neq H$.

Compound 3b can be converted to a compound of formula (I) by the steps outlined in Scheme 1.

EXAMPLES

Example 1

Step A:

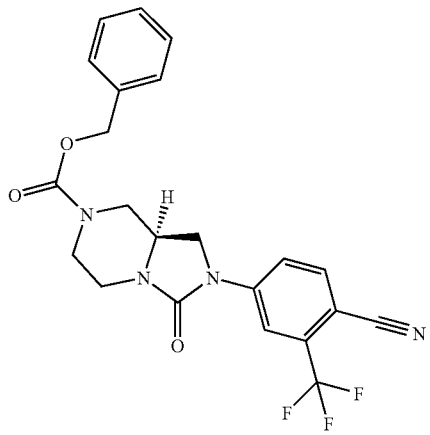
(1A)

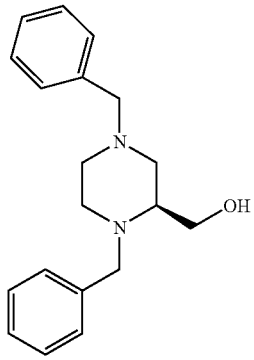
(1B)

To a solution of N,N-dibenzylethylenediamine (30 mL, 127 mmol), K₂CO₃ (120 g, 869 mmol) and EtOH (500 mL) was added R-(−)-epichlorohydrin (9.9 mL, 127 mmol). The mixture was heated at 90° C. for 5 h and then stirred at RT for 14 h. The mixture was filtered with EtOH rinsing, then concentrated in vacuo. The resulting crude piperazine was purified by flash chromatography on silica eluting with 0-10% of a solution of 10% NH₄OH/CH₂Cl₂ in CH₂Cl₂ to give N,N-dibenzyl-(S)-piperazin-2-ylmethanol (1A) as a yellow oil (16 g).

Step B:

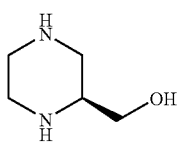

The N,N-dibenzyl-(S)-piperazin-2-ylmethanol (1A, 16 g) was dissolved in MeOH (400 mL) and 10% Pd/C (12 g, DeGussa) was added. Hydrogen was introduced via a balloon, and the reaction was stirred for 20 h. The mixture was filtered through Celite with MeOH rinsing and concentrated to give 6.2 g of (S)-piperazin-2-ylmethanol (1B) as a yellow solid. LC-MS [M+H]⁺=117.28.

Step C:

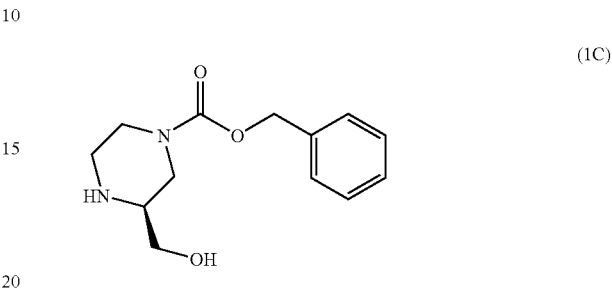
(1C)

To a solution of compound 1B (207 mg, 1.78 mmol) in CH₃CN/DMA/H₂O (1 mL, 0.3 mL, 0.7 mL) cooled to 0° C. was added dropwise CBZ-OSu (444 mg, 1.78 mmol) in DMA (0.5 mL). The reaction was stirred for 15 min at 0° C. then slowly warmed to RT. To the reaction was added H₂O (30 mL) and sat'd NaHCO₃ (5 mL), and then the product was extracted three times with EtOAc (20 mL). The combined EtOAc layers were washed twice with brine, dried over MgSO₄ then concentrated in vacuo to give crude (S)-benzyl 3-(hydroxymethyl)piperazine-1-carboxylate (256 mg). HPLC RT: 1.082 min (4 min Chromolith column TFA). (M+H)⁺:251.

Step D:

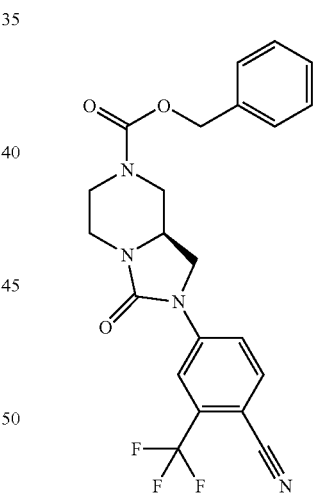

To (S)-benzyl 3-(hydroxymethyl)piperazine-1-carboxylate (256 mg, 1.02 mmol) in DMA (1 mL) was added phenyl 4-cyano-3-(trifluoromethyl)phenylcarbamate (250 mg, 0.82 mmol), and the mixture was heated to 40° C. for 5 h. The reaction was cooled to RT, and PPh₃ (321 mg, 1.22 mmol) followed by DIAD (241 µL, 1.22 mmol) were added to the reaction. After stirring for 15 min at RT, the reaction was diluted with EtOAc (20 mL) and washed twice with 0.5 N NaOH (10 mL), then twice with sat'd brine (10 mL). The EtOAc was dried over MgSO₄ then concentrated in vacuo. The residue was taken up in CH₂Cl₂ (5 mL) and cooled to −10° C., and Et₂O (5 mL) was added. The resulting precipitate was collected by filtration and rinsed with cold 1:1 Et₂O:

CH$_2$Cl$_2$ to give Example 1, (R)-benzyl 2-(4-cyano-3-(trifluoromethyl)phenyl)-3-oxo-hexahydroimidazo[1,5-a]pyrazine-7(1H)-carboxylate 187 mg (52%). HPLC RT: 3.253 min (Chromolith SpeedROD 4.6×50 mm, 10-90% aqueous MeOH over 4 minutes containing 0.1% TFA, 4 ml/min, monitoring at 220 nm). (M+H)$^+$:445.

Example 2

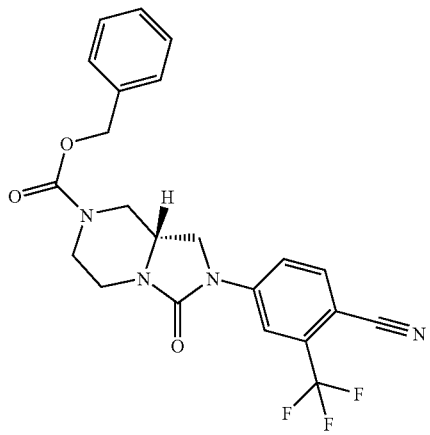

The above compound of Example 2 was prepared following the same procedure described above for Example 1 but starting with S-(–)-epichlorohydrin in Step A. HPLC RT: 3.253 min (Chromolith SpeedROD 4.6×50 mm, 10-90% aqueous MeOH over 4 minutes containing 0.1% TFA, 4 ml/min, monitoring at 220 nm). (M+H)$^+$:445.

Example 3

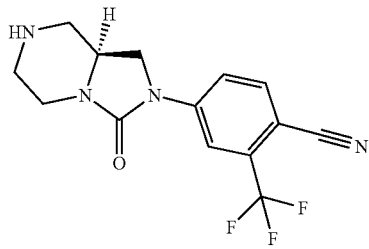

To a solution of Example 1 (0.020 g, 0.045 mmol) in MeOH (5 mL) was added Degussa-type Pd/C (10% Pd, 0.010 g). The resulting reaction mixture was stirred under H$_2$Balloon for 1 h then it was filtered through Celite and the filtrate was concentrated in vacuo to give 0.012 g of Example 3 as a white solid. HPLC: 98% at 1.712 min (retention times) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z 311.18 [M+H]$^+$.

Example 4

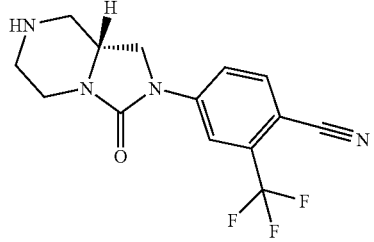

The above amine of Example 4 was prepared following the same procedure described above for Example 3 but with Example 2 as the starting material instead of Example 1. HPLC: 98% at 1.712 min (retention times) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z 311.18 [M+H]$^+$.

Example 5

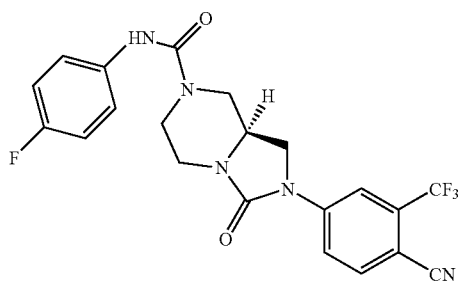

To a colorless solution of the amine of Example 3 (0.100 g; 0.32 mmol) in 2.0 mL dry DCM at RT under nitrogen atmosphere was added 4-fluorophenyl isocyanate (0.055 mL; 0.48 mmol) via syringe. Product precipitated out immediately as a white solid. After 20 min, the suspension was concentrated in vacuo and the resulting off-white solid was purified by flash column chromatography (SiO$_2$; 20-30% ethyl acetate/hexanes to remove impurity, then 80% ethyl acetate/hexanes to elute the title compound as a colorless band). This gave the desired urea (0.133 g, 93%) obtained as a white solid. HPLC (YMS S5 ODS 4.6×50 mm column; 4 minute linear gradient from 10-90% aqueous MeOH with 0.2% H₃PO₄ at 4 mL/min, irradiating at 220 nm): >99% at 3.210 minutes; LCMS: [M+H]⁺=448.1.

Example 6

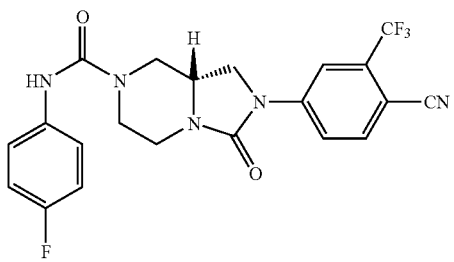

The above compound of Example 6 was prepared following the same procedure described above for Example 5 but starting with Example 4 as starting material instead of Example 3. HPLC (YMS S5 ODS 4.6×50 mm column; 4 minute linear gradient from 10-90% aqueous MeOH with 0.2% H₃PO₄ at 4 mL/min, irradiating at 220 nm): >99% at 3.210 minutes; LCMS: [M+H]⁺=448.1.

Example 7

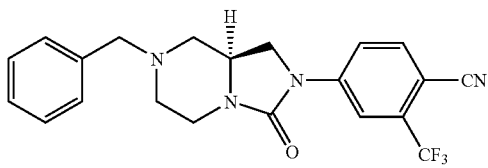

To a solution Example 3 (110.0 mg, 0.36 mmol) in CH₂Cl₂ (5 mL) was added Hünig's base (0.124 mL, 0.71 mmol) followed by benzyl chloride (0.082 mL, 0.71 mmol). The reaction was stirred under N₂ at 22° C. for 30 min. Then it was purified with flash chromatography in ISCO using 12 g column, Flow rate: 30 mL/min, solvent A: CH₂Cl₂, solvent B: EtOAc. Gradient: 0% B to 50% B in 25 minutes to give 0.13 g of Example 7 as a white solid in 88% yield. HPLC: 98% at 3.015 min (retention times) (YMC ODS-A column 4.6×50 mm eluting with 10-90% aqueous MeOH over 4 minutes containing 0.1% H₃PO₄, 4 mL/min, monitoring at 220 nm). MS (ES): m/z 473.06 [M−H+ OAc]⁺.

Example 8

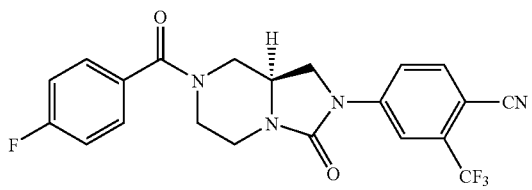

To a solution of Example 3 (25.0 mg, 0.36 mmol) in DMF (1 mL) was added potassium carbonate (45.0 mg, 0.32 mmol) followed by 4-Fluorobenzoyl chloride (0.020 mL, 0.16 mmol). The reaction was stirred at 130° C. for 1 h. Then it was purified with preparative HPLC to give 0.029 g of Example 8 as a white solid in 85% yield. HPLC: 98% at 2.26 min (retention times) (YMC ODS-A column 4.6×50 mm eluting with 10-90% aqueous MeOH over 4 minutes containing 0.1% H₃PO₄, 4 mL/min, monitoring at 220 nm). MS (ES): m/z 473.06 [M+H]⁺419.10

Example 9

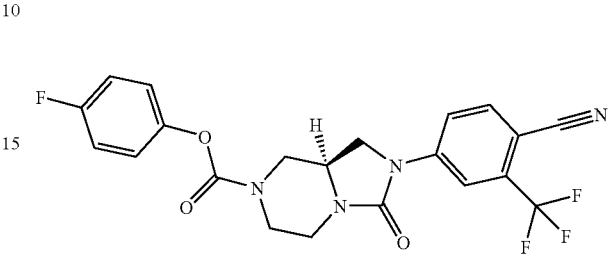

To a solution of Example 3 (0.120 g, 0.39 mmol) in methylene chloride (5.0 mL) at 0° C. was added DIPEA (0.136 mL, 0.78 mmol) and 4-fluorophenylchloroformate (0.066 mL, 0.505 mmol). The solution was warmed to rt, stirred for 1 h, then diluted with methylene chloride and washed once with 1 N NaOH (10 mL), once with brine (10 mL) and dried over anhydrous Na₂SO₄. The crude material was purified by flash chromatography on silica eluting with 0-5% acetone in methylene chloride to give Example 9 (0.151 g) as a white solid. HPLC: 95% at 3.311 minutes (retention time) (YMC ODS-A column 4.6×50 mm eluting with 10-90% aqueous MeOH over 4 minutes containing 0.1% H₃PO₄, 4 mL/min, monitoring at 220 nm). MS (ES): m/z 449.09 [M+H]⁺.

Example 10

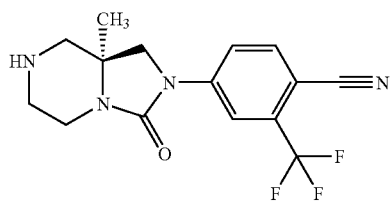

Step A:

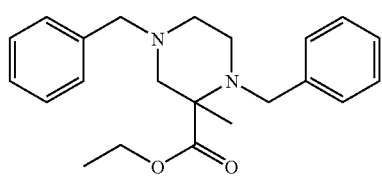

(10A)

To ethyl 1,4-dibenzylpiperazine-2-carboxylate (35.4 g, 0.1 mol) in THF(200 mL) cooled to −78° C. was added dropwise LDA (64 mL, 1.8 M). The reaction was stirred at −78° C. for 1 h then MeI (7.2 mL, 0.11 mol) was added. The reaction was allowed to slowly warm to RT then quenched with sat'd NH₄Cl. Water (200 mL) was added and the residue was extracted with EtOAc (200 mL). The EtOAc layer was washed twice with water then the solvent was removed in vacuo. Silica gel chromatography provided ethyl 1,4-dibenzyl-2-methylpiperazine-2-carboxylate (compound 10A) 14.91 g. HPLC RT: 2.42 min (Chromolith SpeedROD 4.6×50 mm, 10-90% aqueous MeOH over 4 minutes containing 0.1% TFA, 4 ml/min, monitoring at 220 nm). (M+H)$^+$:353.

Step B:

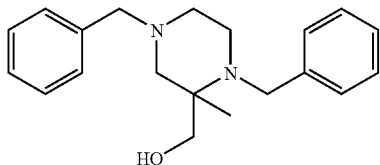
(10B)

To ethyl 1,4-dibenzyl-2-methylpiperazine-2-carboxylate (10A) (14.91 g, 0.042 mol) in THF (70 mL) cooled to 0° C. was slowly added LiAlH$_4$ (70 mL, 1 M). The reaction was warmed to RT for 20 min then cooled to 0° C. and very slowly quenched with Na$_2$SO$_4$.10H$_2$O (32 g, 0.1 mol) followed by addition of Celite (25 g). The mixture was warmed to RT and stirred for 1 hour then the mixture was filtered and the solvents removed in vacuo. The crude (1,4-dibenzyl-2-methylpiperazin-2-yl)methanol (10B), was used in the next step without purification. HPLC RT: 1.34 min (Chromolith SpeedROD 4.6×50 mm, 10-90% aqueous MeOH over 4 minutes containing 0.1% TFA, 4 ml/min, monitoring at 220 nm).

Step C:

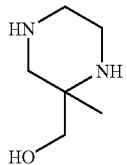
(10C)

To crude (1,4-dibenzyl-2-methylpiperazin-2-yl)methanol (10B), dissolved in MeOH (100 mL) was added under inert atmosphere Pd(OH)$_2$/C (5 g). The mixture was stirred under H$_2$ balloon for 2.5 h then filtered through a 0.45 μm Teflon filter membrane with MeOH rinse. The solvent was removed in vacuo and the crude (2-methylpiperazin-2-yl)methanol (10 C), was used in the next step without further purification.

Step D:

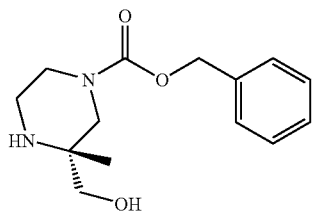
(10D)

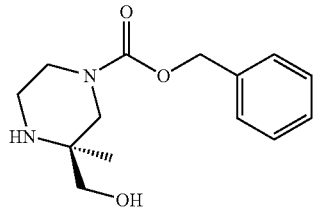
(10E)

To crude (2-methylpiperazin-2-yl)methanol (10 C) (0.042 mol) dissolved in CH$_3$CN/DMA/H$_2$O (20 mL, 20 mL, 20 mL) cooled to 0° C. was added CBZ-OSu (9.5 g, 0.038 mol) in DMA (15 mL). The reaction was stirred at 0° C. for 30 min then warmed to RT. To the mixture was added H$_2$O (500 mL), sat'd brine (50 mL) and 1M NaOH (50 mL), then the residue was extracted four times with EtOAc (100 mL). The combined EtOAc layers were washed twice with brine then dried over MgSO$_4$ and the solvent removed in vacuo to give racemic benzyl 3-(hydroxymethyl)-3-methylpiperazine-1-carboxylate (9.7 g). HPLC RT: 1.302 min (4 min Chromolith column TFA).

The individual enantiomers of benzyl 3-(hydroxymethyl)-3-methylpiperazine-1-carboxylate hydrochloride (1.91 g) were separated on a Chiralpak AD column eluting with 10% i-PrOH in hexane with 0.05% DEA. The separated peaks were concentrated in vacuo to give 10D, (R)-benzyl 3-(hydroxymethyl)-3-methylpiperazine-1-carboxylate 0.795 g, (9.16 min Chiralpak AD column 15% IPA/heptane 0.05% DEA >99% ee) and 10E, (S)-benzyl 3-(hydroxymethyl)-3-methylpiperazine-1-carboxylate (10.10 min Chiralpak AD column 15% IPA/heptane 0.05% DEA 87% ee).

Step E:

Example 10

Example 10 was made starting with Example 10E and following the procedures reported in Examples 1 and 3. HPLC RT: 1.89 min (Chromolith SpeedROD 4.6×50 mm, 10-90% aqueous MeOH over 4 minutes containing 0.1% TFA, 4 ml/min, monitoring at 220 nm). (M+H)$^+$:325.

Example 11

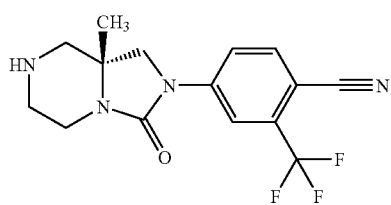

Example 11 was made starting with Example 10D and following the procedures reported in Examples 1 and 3. HPLC RT: 1.89 min (Chromolith SpeedROD 4.6×50 mm, 10-90% aqueous MeOH over 4 minutes containing 0.1% TFA, 4 ml/min, monitoring at 220 nm). (M+H)$^+$:325. The HBr salt of Example 11 (30 mg) was stirred in sat'd aq. NaHCO$_3$ and extracted with EtOAc. The EtOAc layer was washed with sat'd aq. NaHCO$_3$ and dried over MgSO$_4$, then the solvent was removed in vacuo to give the free base (R)-4-(8a-methyl-3-oxo-tetrahydroimidazo[1,5-a]pyrazin-2(1H, 3H,5H)-yl)-2-(trifluoromethyl)benzonitrile (17.3 mg). To a sample of the free base (4.1 mg, 0.013 mmol) dissolved in MeOH (3 mL) was added O,O'-L-dibenzoyltartaric acid (3.5 mg, 0.01 mmol) and the mixture was heated to reflux until all compound dissolved. The mixture was cooled to RT, and the crystals that formed were used to determine the absolute configuration of Example 11 by single crystal x-ray analysis.

Example 12

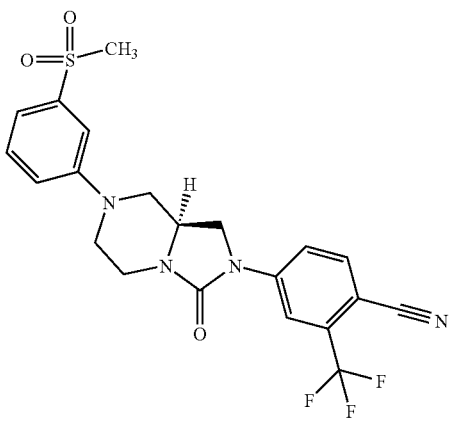

Example 3 (0.060 g, 0.19 mmol), cesium carbonate (0.102 g, 0.29 mmol), 3-bromophenylmethylsulfone (0.063 g, 0.27 mmol), 9,9-dimethyl-4,5-bis(diphenylphosphino)xanthene (0.011 g, 0.019 mmol) and Tris(dibenzylideneacetone)dipalladium (0) (0.009 g, 0.010 mmol) were added to a vial and purged with nitrogen. 1,4-Dioxane (0.2 mL) was added followed by sealing of the vial with a screw cap. The mixture was heated at 100° C. for 4 h, cooled to rt and diluted with EtOAc followed by washing once with brine and drying over anhydrous magnesium sulfate. Purification by flash chromatography on silica eluting with 0-3% acetone in methylene chloride gave 0.073 g of Example 12 as a white solid. HPLC: >99% at 3.016 minutes (retention time) (YMC ODS-A column 4.6×50 mm eluting with 10-90% aqueous MeOH over 4 minutes containing 0.1% $H_3PO_4$, 4 mL/min, monitoring at 220 nm). MS (ES): m/z 523.18 [M–H]$^-$+OAc.

Example 13

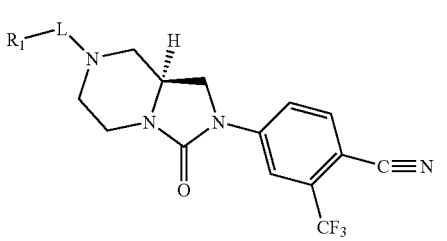

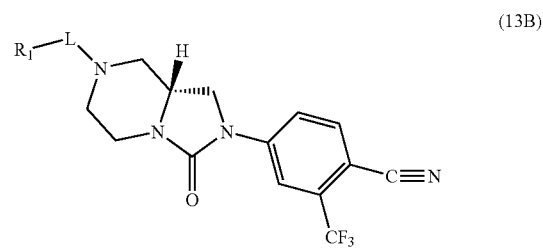

Compounds having the formulae 13A and 13B above, wherein the groups $R_1$ and L, considered together, have the values reported in Table 1, were prepared.

The compounds of Table 1 can be prepared by using Examples 3 or 4, above, as starting material (Example 3 or 4 being selected depending on the desired stereochemistry), and then coupling an appropriate amide, alkanoyl, carboxamide, carboxylic acid, sulfonamide, substituted alkyl (or other $R_1$-L- group), applying standard amine-coupling techniques known in the field and/or as shown above in Examples 5 to 9 and/or as otherwise described herein.

TABLE 1

| Example No. | Formula | $R_1$—L— | Retention Time Min./ Molecular Mass |
|---|---|---|---|
| 13A-1 | 13A | cyclohexyl-CH2CH2- | 2.22 LCMS [M + H]$^+$ = 421.16 |
| 13B-1 | 13B | cyclohexyl-CH2CH2- | 2.21 LCMS [M + H]$^+$ = 421.16 |
| 13A-2 | 13A | cyclohexyl-CH2- | 2.22 LCMS [M + H]$^+$ = 407.15 |
| 13B-2 | 13B | cyclohexyl-CH2- | 2.22 LCMS [M + H]$^+$ = 407.15 |
| 13A-3 | 13A | 4-F-C6H4-CH2CH2- | 2.30 LCMS [M + H]$^+$ = 433.11 |
| 13B-3 | 13B | 4-F-C6H4-CH2CH2- | 2.30 LCMS [M + H]$^+$ = 433.11 |

TABLE 1-continued
| Example No. | Formula | R₁—L— | Retention Time Min./ Molecular Mass |
|---|---|---|---|
| 13A-4 | 13A | 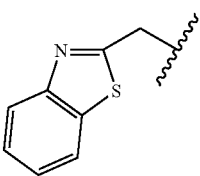 | 3.49 LCMS [M + H]⁺ = 458.07 |
| 13B-4 | 13B | 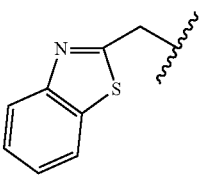 | 3.49 LCMS [M + H]⁺ = 458.07 |
| 13A-5 | 13A | 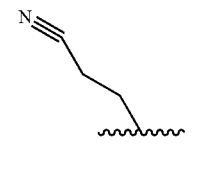 | 2.05 LCMS [M + H]⁺ = 364.12 |
| 13B-5 | 13B | 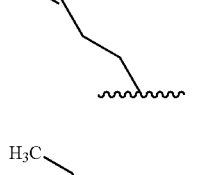 | 2.05 LCMS [M + H]⁺ = 364.12 |
| 13A-6 | 13A | 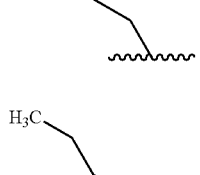 | 1.94 LCMS [M + H]⁺ = 367.08 |
| 13B-6 | 13B | 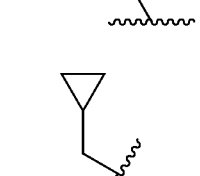 | 1.94 LCMS [M + H]⁺ = 367.08 |
| 13A-7 | 13A | 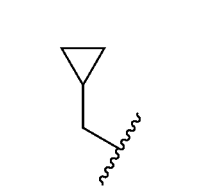 | 1.81 LCMS [M + H]⁺ = 365.02 |
| 13B-7 | 13B |  | 1.81 LCMS [M + H]⁺ = 365.02 |
TABLE 1-continued
| Example No. | Formula | R₁—L— | Retention Time Min./ Molecular Mass |
|---|---|---|---|
| 13A-8 | 13A | 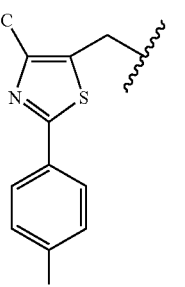 | 3.745 LCMS [M + H]⁺ = 566.08 |
| 13A-9 | 13A | 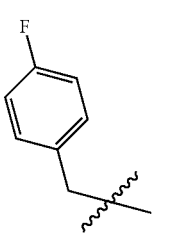 | 2.260 LCMS [M + H]⁺ = 419.10 |
| 13B-9 | 13B | 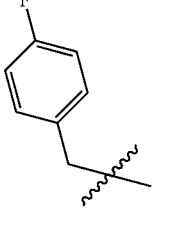 | 2.260 LCMS [M + H]⁺ = 419.10 |
| 13A-10 | 13A | 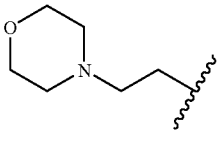 | 1.90 LCMS [M + H]⁺ = 424.28 |
| 13A-11 | 13A | 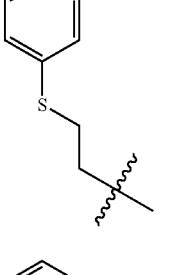 | 2.619 LCMS [M + H]⁺ = 447.10 |
| 13B-11 | 13B | 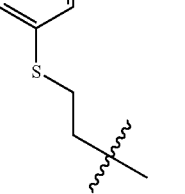 | 2.619 LCMS [M + H]⁺ = 447.10 |

TABLE 1-continued

| Example No. | Formula | R₁—L— | Retention Time Min./ Molecular Mass |
|---|---|---|---|
| 13A-12 | 13A | (pentafluoro ketone group) | 3.50 LCMS [M − H]⁻ = 505.13 |
| 13B-12 | 13B | (pentafluoro ketone group) | 3.50 LCMS [M − H]⁻ = 505.07 |
| 13A-13 | 13A | (isopropyl ketone group) | 2.90 LCMS [M − H]⁻ = 379.11 |
| 13B-13 | 13B | (isopropyl ketone group) | 2.91 LCMS [M − H]⁻ = 379.11 |
| 13A-14 | 13A | (phenyl ketone group) | 3.10 LCMS [M − H]⁻ = 413.15 |
| 13B-14 | 13B | (phenyl ketone group) | 3.02 LCMS [M − H]⁻ = 413.08 |
| 13A-15 | 13A | (4-fluorobenzyl amide group) | 3.24 LCMS [M + H]⁺ = 462.1 |
| 13B-15 | 13B | (4-fluorobenzyl amide group) | 3.24 LCMS [M + H]⁺ = 462.1 |
| 13A-16 | 13A | (isopropyl amide group) | 2.936 LCMS [M + H]⁺ = 396.1 |
| 13B-16 | 13B | (isopropyl amide group) | 2.938 LCMS [M + H]⁺ = 396.1 |
| 13A-17 | 13A | (2-methoxyphenyl cyanamidine group) | 3.02 LCMS [M + H]⁺ = 484.16 |
| 13A-18 | 13A | (4-chlorophenyl cyanamidine group) | 3.27 LCMS [M + H]⁺ = 488.1 |
| 13B-18 | 13B | (4-chlorophenyl cyanamidine group) | 3.27 LCMS [M + H]⁺ = 488.1 |
| 13A-19 | 13A | (4-fluorophenyl amide group) | 3.208 LCMS [M + H]⁺ = 448.3 |
| 13B-19 | 13B | (4-fluorophenyl amide group) | 3.210 LCMS [M + H]⁺ = 448.3 |
| 13A-20 | 13A | (isobutyl ester group) | 3.593 LCMS [M − H]⁻ = 423.1 |

TABLE 1-continued

| Example No. | Formula | R₁—L— | Retention Time Min./Molecular Mass |
|---|---|---|---|
| 13B-20 | 13B | (H₃C)₂CHCH₂-O-C(=O)- | 3.591 LCMS [M − H]⁻ = 423.1 |
| 13A-21 | 13A | H₃CCH₂-O-C(=O)- | 3.10 LCMS [M − H]⁻ = 381.11 |
| 13B-21 | 13B | H₃CCH₂-O-C(=O)- | 3.10 LCMS [M − H]⁻ = 381.11 |
| 13A-22 | 13A | 4-F-C₆H₄-O-C(=O)- | 3.32 LCMS [M − H]⁻ = 447.09 |
| 13B-22 | 13B | 4-F-C₆H₄-O-C(=O)- | 3.11 LCMS [M − H]⁻ = 447.12 |
| 13A-23 | 13A | C₆H₅-O-C(=O)- | 3.30 LCMS [M + H]⁺ = 431.14 |
| 13B-23 | 13B | C₆H₅-O-C(=O)- | 3.30 LCMS [M + H]⁺ = 431.14 |
| 13A-24 | 13A | 2-pyridyl-C(=O)- | 2.70 LCMS [M + H]⁺ = 416.1 |
| 13B-24 | 13B | 2-pyridyl-C(=O)- | 2.70 LCMS [M + H]⁺ = 416.1 |

TABLE 1-continued

| Example No. | Formula | R₁—L— | Retention Time Min./Molecular Mass |
|---|---|---|---|
| 13A-25 | 13A | ethyl | 1.720 LCMS [M + H]⁺ = 339.2 |
| 13A-26 | 13A | n-propyl | 1.80 LCMS [M + H]⁺ = 353.32 |
| 13A-27 | 13A | benzyl | 2.188 LCMS [M + H]⁺ = 401.31 |
| 13A-28 | 13A | 2-oxazolylmethyl | 2.52 LCMS [M + H]⁺ = 392.26 |

To a solution of Example 3 (0.030 g, 0.097 mmol) in DMF (0.5 mL) was added 4,6-dichloropyrimidine (0.029 g, 0.194 mmol) and the reaction heated to 130° C. for 1.5 h. The crude mixture was then cooled to 22° C. and purified by preparative HPLC to afford 0.032 g of Example 14 as a white solid. HPLC: >99% at 3.145 minutes (retention time) (YMC ODS-A column 4.6×50 mm eluting with 10-90% aqueous MeOH over 4 minutes containing 0.1% H₃PO₄, 4 mL/min, monitoring at 220 nm). MS (ES): m/z 423.04 [M+H]⁺.

Example 15

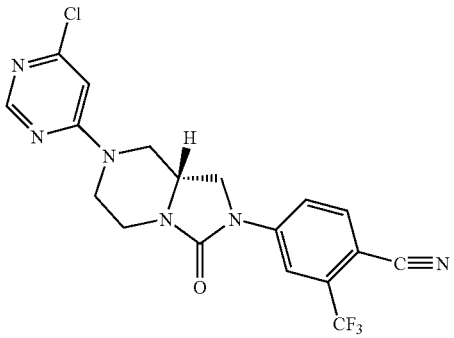

The above compound Example 15 was prepared using the same procedure described above for Example 14 using Example 4 as the starting material. HPLC: >99% at 3.145 minutes (retention time) (YMC ODS-A column 4.6×50 mm eluting with 10-90% aqueous MeOH over 4 minutes containing 0.1% H₃PO₄, 4 mL/min, monitoring at 220 nm). MS (ES): m/z 423.04 [M+H]⁺.

Example 16

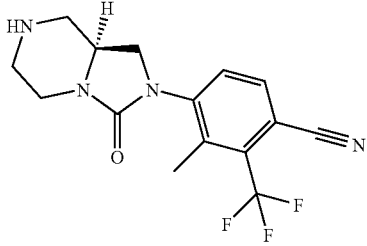

Example 16 was prepared by the procedures reported in Examples 1 and 3 using 4-amino-5-methyl-6-trifluoromethylbenzonitrile as the starting aniline. HPLC t$_R$=1.50 min (YMC S5 ODS 4.6×50 mm, 10-90% aqueous MeOH containing 0.2% H₃PO₄, 4 min gradient, monitored at 220 nm). [M+H]⁺=352.12.

Example 17

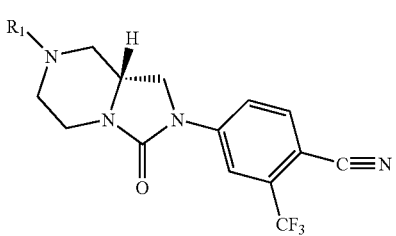
(17A)

-continued

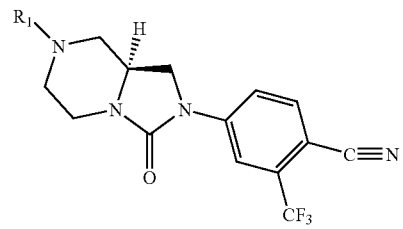
(17B)

Compounds having the above formulae 17A and 17B, wherein the group R₁ has the values reported in Table 2, were prepared using Example 3 or 4 as starting material and following the same or similar procedures as described above for Examples 12 and 14 to 15.

TABLE 2

| Example No. | Formula | R₁— | Retention Time Min./Molecular Mass |
|---|---|---|---|
| 17A-1 | 17A | ![structure with CN and F₃C on benzene] | 3.46 LCMS [M − H]⁻ = 478.1 |
| 17B-1 | 17B | ![structure with CN and F₃C on benzene] | 3.46 LCMS [M − H]⁻ = 478.1 |

Example 18

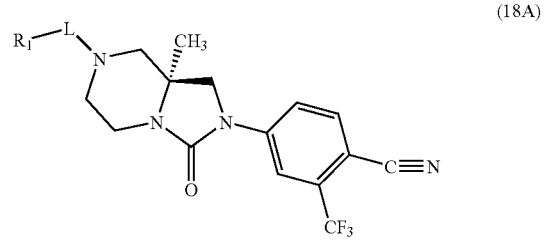
(18A)

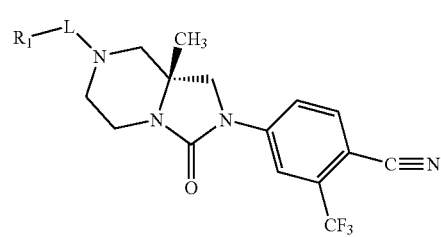
(18B)

Compounds having the formulae 18A and 18B above, wherein the groups R₁ and L, considered together, have the values reported in Table 3, were prepared. The compounds of Table 3 can be prepared by using Examples 11 or 12 above, as starting material (Example 11 or 12 being selected depending on the desired stereochemistry), and then coupling an appropriate amide, alkanoyl, carboxamide, carboxylic acid, sulfonamide, substituted alkyl (or other R₁-L- group), applying standard amine-coupling techniques known in the field and/or as shown above in Examples 5 to 9 and/or as otherwise described herein.

TABLE 3

| Example No. | Formula | R₁—L— | Retention Time Min./Molecular Mass |
|---|---|---|---|
| 18A-1 | 18A | 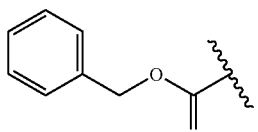 | 3.36 LCMS [M + H]⁺ = 459 |
| 18B-1 | 18B | 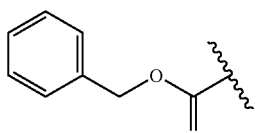 | 3.36 LCMS [M + H]⁺ = 459 |
| 18A-2 | 18A | 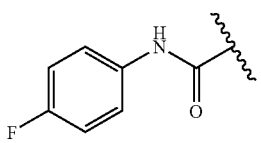 | 3.076 LCMS [M + H]⁺ = 462 |
| 18B-2 | 18B | 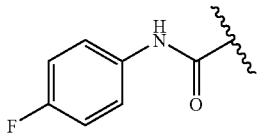 | 3.076 LCMS [M + H]⁺ = 462 |

Example 19

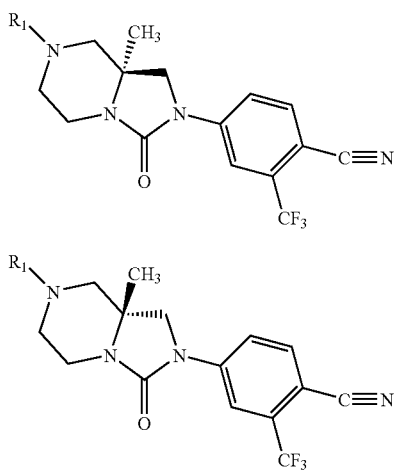

(19A)

(19B)

Compounds having the above formulae 19A and 19B, wherein the group R₁ has the values reported in Table 4, were prepared starting with Examples 11 or 12 and following the same or similar procedures as described above for Examples 12, 14 to 15.

TABLE 4

| Example No. | Formula | R₁— | Retention Time Min./Molecular Mass |
|---|---|---|---|
| 19A-1 | 19A | 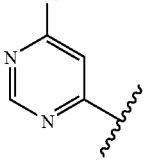 | 2.991 LCMS [M+H]⁺= 437 |
| 19B-1 | 19B | 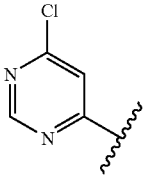 | 2.991 LCMS [M+H]⁺= 437 |

Example 20

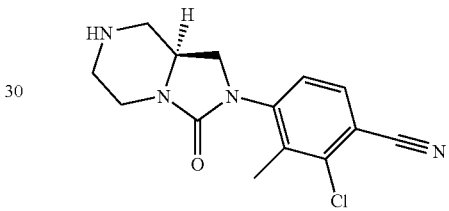

The above compound Example 20 was prepared following the same or similar process described above for Example 2, except 3-chloro-4-cyano-1-methylphenyl carbamate was used in the first step in place of 4-cyano-3-(trifluoromethyl)phenyl carbamate. HPLC $t_R$=1.46 min (YMC S5 ODS 4.6×50 mm, 10-90% aqueous MeOH containing 0.2% $H_3PO_4$, 4 min gradient, monitored at 220 nm). [M+H]⁺=291.1.

Example 21

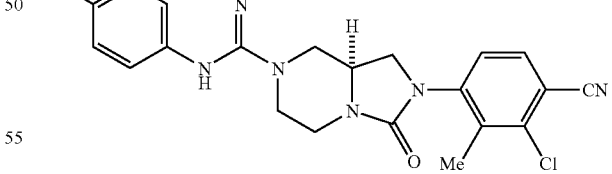

A solution of Example 20 (50 mg, 0.17 mmol) in DMF (1 mL) was treated with 1-(4-chlorophenyl)-3-cyanothiourea (54 mg, 0.26 mmol), followed by EDC (49 mg, 0.26 mmol). The reaction mixture was stirred at room temperature for three hours, diluted with EtOAc (5 mL) and washed with 1N citric acid (2×5 mL). The organic layer was further washed with 10% LiCl (5 mL), dried ($Na_2SO_4$), filtered and concentrated. The crude material was triturated with MeOH to afford Example 21 (42 mg, 53%). HPLC $t_R$=3.187 min (YMC S5

ODS 4.6×50 mm, 10-90% aqueous MeOH containing 0.2% $H_3PO_4$, 4 min gradient, monitored at 220 mm). $[M+H]^+$ =468.09.

Example 22

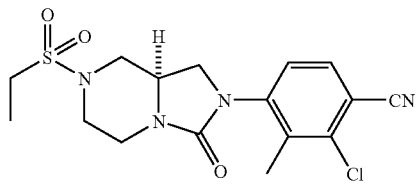

A solution of Example 20 (35 mg, 0.12 mmol) in $CH_2Cl_2$ (5 mL) at 0° C. was treated with DIPEA (0.024 mL, 0.14 mmol), followed by a solution of ethylsulfonyl chloride (0.014 mL, 0.14 mmol). The reaction mixture was warmed to room temperature and stirred for ten minutes. The resulting mixture was concentrated to dryness and purified by preparative reverse-phase HPLC (YMC ODS-A 20×100 mm, 10-90% aqueous MeOH containing 0.1% TFA, 20 min gradient, 20 mL/min flow rate, monitored at 220 nm) to afford Example 22 (22 mg, 48%). HPLC $t_R$=2.578 min (YMC S5 ODS 4.6×50 mm, 10-90% aqueous MeOH containing 0.2% $H_3PO_4$, 4 min gradient, monitored at 220 nm). $[M+H]^+$=383.18.

Example 23

(S)-2-(3-chloro-4-cyano-2-methylphenyl)-N-(4-(4-(ethylsulfonyl)piperazin-1-yl)butyl)-3-oxo-hexahydroimidazo[1,5-a]pyrazine-7(1H)-carboxamide

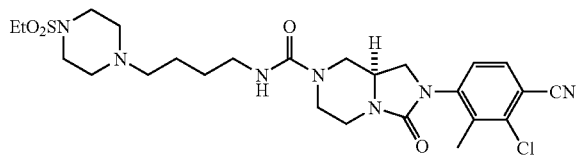

Step A: (S)-ethyl 4-(2-(3-chloro-4-cyano-2-methylphenyl)-3-oxo-octahydroimidazo[1,5-a]pyrazine-7-carboxamido)butanoate (23A)

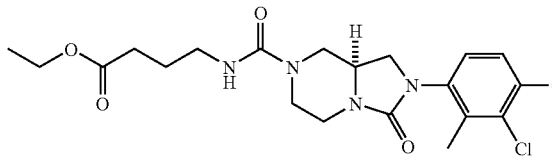

A solution of Example 20 (100 mg, 0.34 mmol) in THF (5 mL) was treated with a solution of ethyl 4-isocyanatobutanoate (60 mg, 0.38 mmol) in THF (1 mL). The reaction mixture was stirred at rt for 2 hr, then concentrated to dryness. The residue was taken up in EtOAc (10 mL) and washed with sat'd aqueous $NaHCO_3$ (2×10 mL). The organic layer was dried ($Na_2SO_4$), filtered and concentrated to Example 23A which was used in further steps without further purification.

Step B: (S)-2-(3-chloro-4-cyano-2-methylphenyl)-N-(4-hydroxybutyl)-3-oxo-hexahydroimidazo[1,5-a]pyrazine-7(1H)-carboxamide (23B)

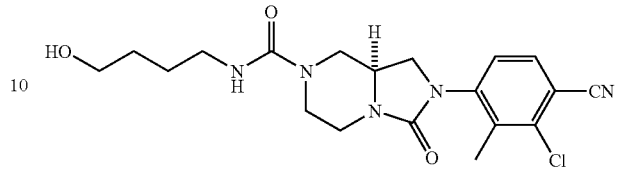

A solution of 23A (70 mg, 0.16 mmol) in THF (5 mL) at −40° C. was treated with $LiBH_4$ (10 mg, 0.47 mmol). The reaction mixture was slowly warmed to room temperature and stirred for 16 hours. Additional $LiBH_4$ (10 mg) was added and the reaction mixture was stirred for an additional six hours. The reaction was quenched with water (20 mL), and then the residue extracted with EtOAc (4×20 mL), dried ($Na_2SO_4$), filtered and concentrated. The crude Example 23B was used in the next step without further purification.

Step C: (S)-4-(2-(3-chloro-4-cyano-2-methylphenyl)-3-oxo-octahydroimidazo[1,5-a]pyrazine-7-carboxamido)butyl methanesulfonate (23C)

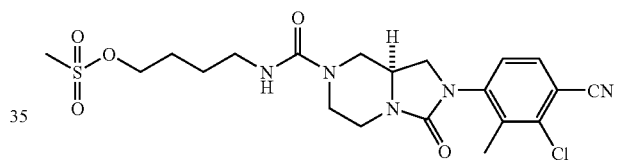

A solution of Example 23B (60 mg, 0.15 mmol) in $CH_2Cl_2$ (5 mL) at 0° C. was treated with $Et_3N$ (0.02 mL, 0.16 mmol) and methanesulfonyl chloride (0.01 mL, 0.26 mmol). The reaction mixture was warmed to room temperature and stirred for 30 minutes. Additional methanesulfonyl chloride (0.01 mL, 0.16 mmol) was added and the reaction was stirred for another 10 minutes. The reaction mixture was concentrated to a yellow film and crude Example 23C was used in the next step without further purification.

Step D: (S)-2-(3-chloro-4-cyano-2-methylphenyl)-N-(4-(4-(ethylsulfonyl)piperazin-1-yl)butyl)-3-oxo-hexahydroimidazo[1,5-a]pyrazine-7(1H)-carboxamide (23)

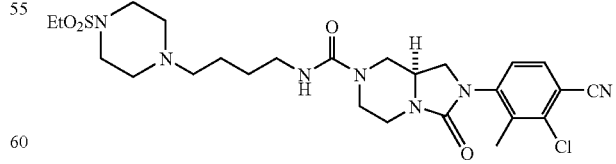

A solution of 23C (30 mg, 0.08 mmol) in acetonitrile (3 mL) was treated with $K_2CO_3$ (40 mg, 0.3 mmol) and 1-(ethylsulfonyl)piperazine (134 mg, 0.75 mmol). The reaction mixture was heated to reflux for 16 hours, then concentrated. The residue was partitioned between EtOAc (10 ml) and water (10 mL). The organic layer was dried (Na$_2$SO$_4$), filtered and concentrated. The crude material was purified by reverse-phase HPLC (YMC ODS-A 20×100 mm, 10-90% aqueous MeOH containing 0.1% TFA, 20 min gradient, 20 mL/min flow rate, monitored at 220 nm) to afford Example 23 (3 mg, 7%). HPLC t$_R$=2.177 min (YMC S5 ODS 4.6×50 mm, 10-90% aqueous MeOH containing 0.2% H$_3$PO$_4$, 4 min gradient, monitored at 220 nm). [M+H]$^+$=566.3.

Example 24

(S)-2-(3-chloro-4-cyano-2-methylphenyl)-N-(4-(4-(ethylsulfonyl)piperazin-1-yl)-4-oxobutyl)-3-oxo-hexahydroimidazo[1,5-a]pyrazine-7(1H)-carboxamide

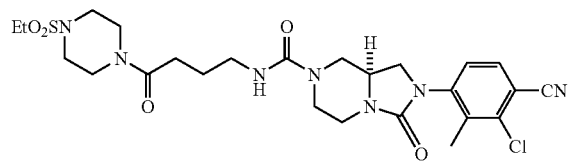

Step A: (S)-4-(2-(3-chloro-4-cyano-2-methylphenyl)-3-oxo-octahydroimidazo[1,5-a]pyrazine-7-carboxamido)butanoic acid (24A)

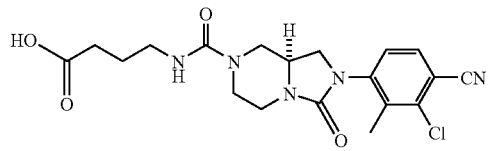

A solution of Example 20 (76 mg, 0.17 mmol) in THF (2 mL) and MeOH (2 mL) was treated with a solution of LiOH.H$_2$O (14 mg, 0.34 mmol) in water (2 mL). The solution was stirred at room temperature for 16 h then lyophilized to a white powder, and the crude 24A was used in the next step without further purification.

Step B: (S)-2-(3-chloro-4-cyano-2-methylphenyl)-N-(4-(4-(ethylsulfonyl)piperazin-1-yl)-4-oxobutyl)-3-oxo-hexahydroimidazo[1,5-a]pyrazine-7(1H)-carboxamide

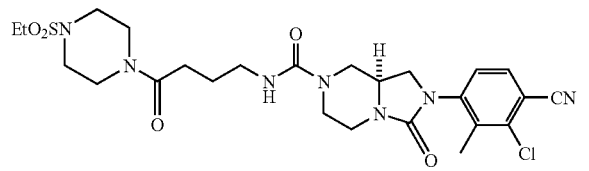

A solution of 24A (35 mg, 0.08 mmol) in DMF (2 mL) was treated with Bop reagent (44 mg, 0.10 mmol), DIPEA (0.017 mL, 0.10 mmol) and 1-(ethylsulfonyl)piperazine (28 mg, 0.16 mmol). The reaction mixture was stirred at room temperature for 1 hr and the solvent removed under reduced pressure. The crude reaction was purified by preparative reverse-phase HPLC (YMC ODS-A 20×100 mm, 10-90% aqueous MeOH containing 0.1% TFA, 20 min gradient, 20 mL/min flow rate, monitored at 220 nm) to afford Example 24 (32 mg, 70%). HPLC t$_R$=2.700 min (YMC S5 ODS 4.6×50 mm, 10-90% aqueous MeOH containing 0.2% H$_3$PO$_4$, 4 min gradient, monitored at 220 nm). [M+H]$^+$=580.17.

Example 25

(S)-2-chloro-4-(7-(6-(4-(ethylsulfonyl)piperazin-1-yl)-6-oxohexyl)-3-oxo-tetrahydroimidazo[1,5-a]pyrazin-2(1H,3H,5H)-yl)-3-methylbenzonitrile

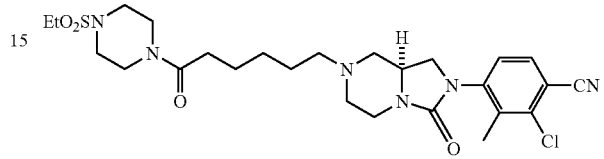

Step A: (S)-methyl 6-(2-(3-chloro-4-cyano-2-methylphenyl)-3-oxo-hexahydroimidazo[1,5-a]pyrazin-7(1H)-yl)hexanoate (25A)

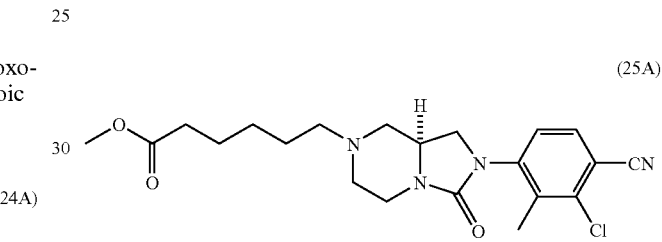

A solution of Example 20 (50 mg, 0.17 mmol) in THF (2 mL) was treated with methyl 6-oxohexanoate (50 mg, 0.34 mmol) and stirred at room temperature for two hours. Sodium triacetoxyborohydride (72 mg, 0.34 mmol) was added and the reaction was stirred for four hours. Additional aldehyde (50 mg) and sodium triacetoxyborohydride (72 mg) were added and the mixture was stirred for 16 hours at room temperature. The reaction was quenched with sat'd aqueous NaHCO$_3$ (10 mL) and extracted with EtOAc (3×10 mL). The combined organic layers were dried (Na$_2$SO$_4$), filtered and concentrated. The crude material was purified by flash chromatography (SiO$_2$, 1% to 5% MeOH/CH$_2$Cl$_2$) to afford 25A as an oil (68 mg, 96%).

Step B: (S)-6-(2-(3-chloro-4-cyano-2-methylphenyl)-3-oxo-hexahydroimidazo[1,5-a]pyrazin-7(1H)-yl)hexanoic acid (25B)

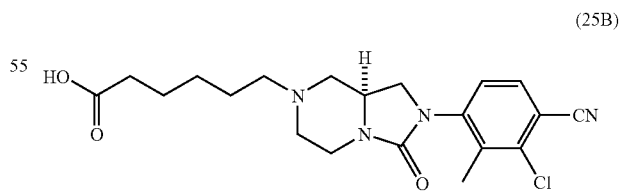

To a solution of 25A (70 mg, 0.17 mmol) in THF (1 mL) and MeOH (1 mL) was added a solution of LiOH.H$_2$O (14 mg, 0.33 mmol) in water (1 mL). The reaction was stirred at room temperature for six hours, then concentrated to dryness. The crude 25B was used in the next step without further purification.

Step C: (S)-2-chloro-4-(7-(6-(4-(ethylsulfonyl)piperazin-1-yl)-6-oxohexyl)-3-oxo-tetrahydroimidazo[1,5-a]pyrazin-2(1H,3H,5H)-yl)-3-methylbenzonitrile

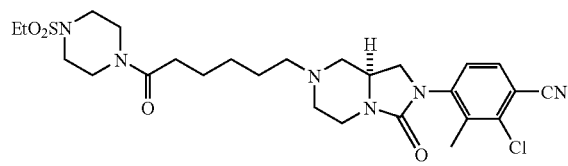

To a solution of Example 25B (70 mg, 0.17 mmol) in DMF (2 mL) at room temperature was added DIPEA (0.035 mL, 0.2 mmol) and 1-(ethylsulfonyl)piperazine (60 mg, 0.34 mmol). Bop reagent (90 mg, 0.2 mmol) was added and the reaction was stirred for two hours. The reaction was diluted with EtOAc (10 mL) and washed with 10% aqueous LiCl (2×10 mL). The organic layer was dried ($Na_2SO_4$), filtered and concentrated. The crude material was purified by preparative reverse-phase HPLC (YMC ODS-A 20×100 mm, 10-90% aqueous MeOH containing 0.1% TFA, 20 min gradient, 20 mL/min flow rate, monitored at 220 nm) to give Example 25 (15 mg). HPLC $t_R$=2.010 min (YMC S5 ODS 4.6×50 mm, 10-90% aqueous MeOH containing 0.2% $H_3PO_4$, 4 min gradient, monitored at 220 nm). $[M+H]^+$=565.29.

Example 26

(S)-2-chloro-4-(7-(6-(4-(ethylsulfonyl)piperazin-1-yl)hexyl)-3-oxo-tetrahydroimidazo[1,5-a]pyrazin-2(1H,3H,5H)-yl)-3-methylbenzonitrile

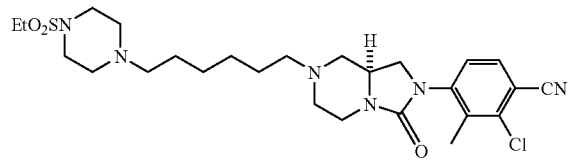

Step A: (S)-4-(7-(6-bromohexyl)-3-oxo-tetrahydroimidazo[1,5-a]pyrazin-2(1H,3H,5H)-yl)-2-chloro-3-methylbenzonitrile (26A)

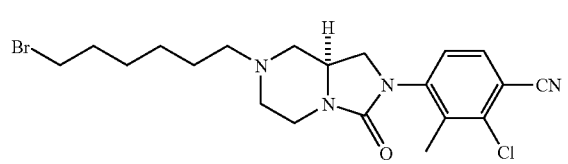

A solution of Example 20 (50 mg, 0.17 mmol) in DMF (5 mL) at 0° C. was treated with a 60% dispersion of NaH in mineral oil (13 mg, 0.34 mmol). The reaction was stirred for 30 minutes and a solution of 1,6-dibromohexane (0.052 mL, 0.34 mmol) in DMF (1 mL) was added. The reaction was warmed to rt and stirred for 48 hours. The mixture was diluted with EtOAc (25 mL) and washed with water (10 mL) and 10% LiCl solution (10 mL). The organic layer was dried ($Na_2SO_4$), filtered and concentrated. The crude bromide was purified by flash chromatography ($SiO_2$, 2.5% MeOH/$CH_2Cl_2$) to afford 26A (42 mg, 55%).

Step B: (S)-2-chloro-4-(7-(6-(4-(ethylsulfonyl)piperazin-1-yl)hexyl)-3-oxo-tetrahydroimidazo[1,5-a]pyrazin-2(1H,3H,5H)-yl)-3-methylbenzonitrile

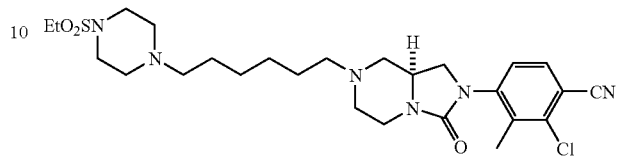

A solution of 26A (40 mg, 0.09 mmol) in acetonitrile (2 mL) was treated with $K_2CO_3$ (18 mg, 0.13 mmol) and 1-(ethylsulfonyl)piperazine (16 mg, 0.09 mmol). The reaction mixture was heated to reflux and stirred for 18 hours. The mixture was then cooled to room temperature and concentrated. The crude material was purified by reverse-phase HPLC (YMC ODS-A 20×100 mm, 10-90% aqueous MeOH containing 0.1% TFA, 20 min gradient, 20 mL/min flow rate, monitored at 220 nm) to afford Example 26 (18 mg, 38%). HPLC $t_R$=1.557 min (YMC S5 ODS 4.6×50 mm, 10-90% aqueous MeOH containing 0.2% $H_3PO_4$, 4 min gradient, monitored at 220 nm). $[M+H]^+$=551.23.

Example 27

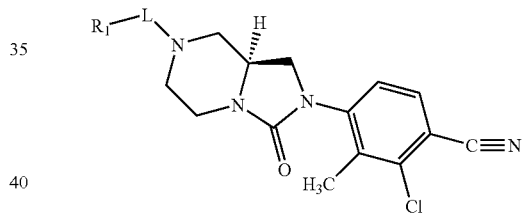

Compounds having the above formula, wherein the groups $R_1$ and L, considered together, have the values reported in Table 5, were prepared. These compounds can be prepared using Example 20 as starting material, then coupling an appropriate functionality following standard coupling techniques known in the field, or as described in Examples 5 to 9 and 21 to 26, or elsewhere herein.

TABLE 5

| Example No. | $R_1$—L— | Retention Time Min./Molecular Mass |
|---|---|---|
| 27-1 | 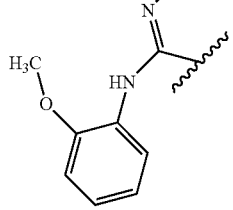 | 2.923 LCMS $[M + H]^+$ = 464.18 |

TABLE 5-continued

| Example No. | R₁—L— | Retention Time Min./Molecular Mass |
|---|---|---|
| 27-2 | (piperidine-propyl-NH-C(O)-) | 2.197 LCMS [M + H]⁺ = 473.3 |
| 27-3 | (piperidine-C(O)-alkyl-) | 2.18 LCMS [M + H]⁺ = 444.24 |
| 27-4 | (piperidine-C(O)-alkyl-) | 2.27 LCMS [M + H]⁺ = 472.4 |
| 27-5 | (ethylsulfonyl-piperazine-alkyl-C(O)-) | 2.17 LCMS [M + H]⁺ = 565 |
| 27-6 | (ethylsulfonyl-piperazine-C(O)-alkyl-NH-C(O)-) | 2.70 LCMS [M + H]⁺ = 580.7 |
| 27-7 | (piperidine-C(O)-alkyl-NH-C(O)-) | 3.02 LCMS [M + H]⁺ = 487.2 |

Example 28

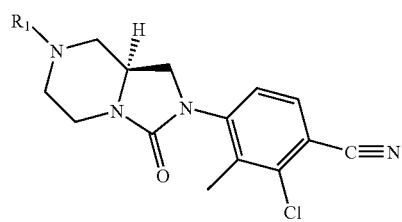

Compounds having the above formula 28, wherein the group R₁ has the values reported in Table 6, were prepared following the same or similar procedure described above for Examples 12 and 14 except that Example 20 was used as starting material.

TABLE 6

| Example No. | R₁— | Retention Time Min./Molecular Mass |
|---|---|---|
| 28-1 | (4-cyano-3-trifluoromethylphenyl-) | 2.29 LCMS [M − H]⁻ = 460.08 |
| 28-2 | (6-chloropyrimidin-4-yl-) | 2.90 LCMS [M − H]⁻ = 403.05 |

Example 29

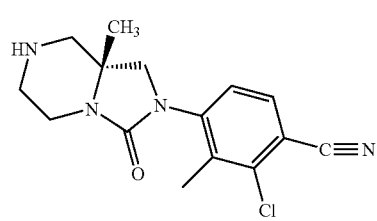

Example 29 was prepared using Example 10D and 2-chloro-3-methyl-4-aminobenzonitrile as starting materials and following the procedures reported for Examples 1C and 3. HPLC RT: 1.55 min (Chromolith SpeedROD 4.6×50 mm, 10-90% aqueous MeOH over 4 minutes containing 0.1% TFA, 4 ml/min, monitoring at 220 nm). (M+H)⁺:305.

Example 30

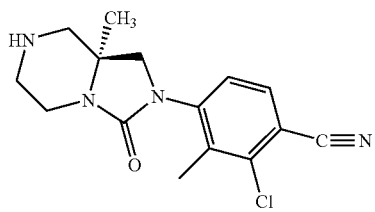

Example 30 was prepared using Example 10E and 2-chloro-3-methyl-4-aminobenzonitrile as starting materials and following the procedures reported for Examples 1C and 3. HPLC RT: 1.54 min (Chromolith SpeedROD 4.6×50 mm, 10-90% aqueous MeOH over 4 minutes containing 0.1% TFA, 4 ml/min, monitoring at 220 nm). (M+H)⁺305.

Example 31

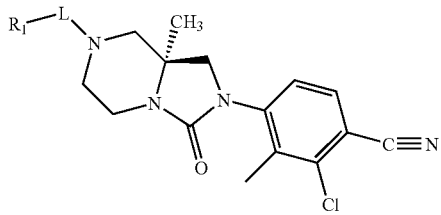

Compounds having the formulae 31A and 31B above, wherein the groups $R_1$ and L, considered together, have the values reported in Table 7, were prepared. The compounds of Table 7 can be prepared by using Examples 29 or 30, above, as starting material (Example 29 or 30 being selected depending on the desired stereochemistry), and then coupling an appropriate amide, alkanoyl, carboxamide, carboxylic acid, sulfonamide, substituted alkyl ($R_1$-L-) group, applying standard amine-coupling techniques known in the field and/or as shown above in Examples 5-9 or 21-26 and/or as otherwise described herein.

TABLE 7

| Example No. | Formula | $R_1$—L— | Retention Time Min./Molecular Mass |
|---|---|---|---|
| 31A-1 | 31A | benzyl ester | 3.148 LCMS [M + H]⁺ = 439 |
| 31B-1 | 31B | benzyl ester | 3.165 LCMS [M + H]⁺ = 439 |
| 31A-2 | 31A | 4-fluorophenyl amide | 2.838 LCMS [M + H]⁺ = 442 |
| 31B-2 | 31B | 4-fluorophenyl amide | 2.486 LCMS [M + H]⁺ = 442 |

Example 32

Compounds having the above formulae 32A and 32B, wherein the group $R_1$ has the values reported in Table 8, were prepared following the same or similar procedure described above for Examples 12 and 14 except that Examples 29 or 30 were used as starting material depending on the desired stereochemistry.

TABLE 8

| Example No. | Formula | R₁—L— | Retention Time Min./Molecular Mass |
|---|---|---|---|
| 32A-1 | 32A | 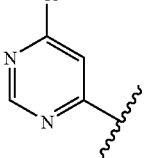 | 2.748 LCMS [M + H]⁺ = 417 |
| 32B-1 | 32B | 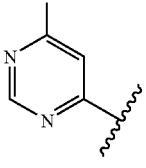 | 2.733 LCMS [M + H]⁺ = 417 |

Example 33

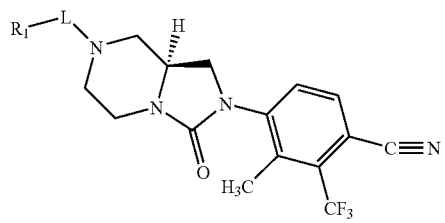

Compounds having the above formula, wherein the groups R₁ and L, considered together, have the values reported in Table 9, were prepared. The compounds of Table 9 can be prepared by using Example 16 as starting material and then coupling an appropriate amide, alkanoyl, carboxamide, carboxylic acid, sulfonamide, substituted alkyl (R₁-L-) group, applying standard amine-coupling techniques known in the field and/or as shown above in Examples 5-9 and/or as otherwise described herein.

TABLE 9

| Example No. | R₁—L— | Retention Time Min./Molecular Mass |
|---|---|---|
| 33-1 | 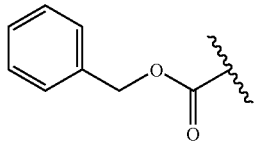 | 3.30 LCMS [M + H]⁺ = 459.13 |
| 33-2 | 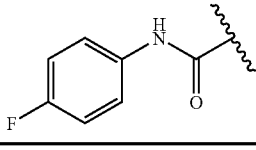 | 3.10 LCMS [M + H]⁺ = 462.26 |

Example 34

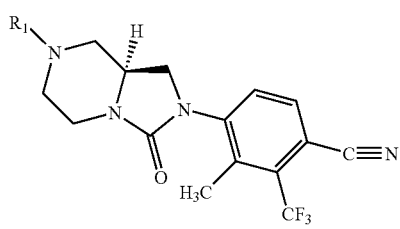

Compounds having the above formula, wherein the group R₁ has the values reported in Table 10, were prepared following the same or similar procedure described above for Examples 12 and 14 except that Example 16 was used as starting material.

TABLE 10

| Example No. | R₁—L— | Retention Time Min./Molecular Mass |
|---|---|---|
| 35-1 | 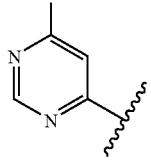 | 3.02 LCMS [M + H]⁺ = 437.05 |
| 35-2 | 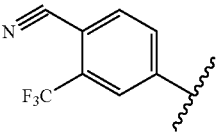 | 3.36 LCMS [M + H]⁺ = 494.29 |

What is claimed is:
1. A compound having the formula (I),

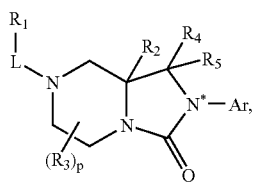

and/or pharmaceutically-acceptable salts thereof, wherein:
Ar is

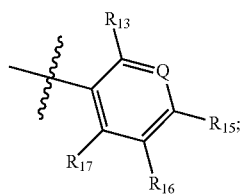

Q is $CR_{14}$; and
$R_{13}$, $R_{14}$, $R_{15}$, $R_{16}$ and $R_{17}$ are independently selected from hydrogen, lower alkyl, halogen, cyano, haloalkyl, haloalkoxy, lower alkoxy, and a lower alkyl substituted with one to two of halogen, cyano, haloalkyl, haloalkoxy, and/or lower alkoxy, provided that one of $R_{13}$, $R_{14}$, $R_{15}$, $R_{16}$ and $R_{17}$ is cyano;

L is $-A_1-N(R_{10})C(=O)-A_2-$, $-A_1-C(=O)N(R_{10})-A_2-$, $-A_1-C(=O)-A_2-$, $-A_1-C(=O)O-A_2-$, $-A_1-OC(=O)-A_2-$, $-A_1-C(=NR_{11})-A_2-$, $-A_1-C(=NR_{11})N(R_{10})-A_2-$, $-A_1-S-A_2-$, $-A_1-NR_{10}-A_2-$, $-A_1-S(O)_2-A_2-$, $-A_1-N(R_{10})S(O)_2-A_2-$, $-A_1-S(O)_2N(R_{10})-A_2-$, or $A_1-A_2-$;

$A_1$ is $—(CR_6R_7)_m—$;

$A_2$ is $—(CR_8R_9)_n—$;

$R_1$ is hydrogen, alkyl, substituted alkyl, aryl, substituted aryl, cycloalkyl, substituted cycloalkyl, heterocyclo, substituted heterocyclo, heteroaryl, or substituted heteroaryl, or when L is $-A_1-A_2-$ or when m is greater than 0, $R_1$ may be cyano;

$R_2$ is hydrogen, lower alkyl, or substituted lower alkyl;

$R_3$ is at each occurrence individually selected from lower alkyl, halogen, cyano, hydroxy, lower alkoxy, trifluoromethyl, trifluoromethoxy, amino, $C_{1-4}$alkylamino, amino$C_{1-4}$alkyl, $—CO_2H$, $—CO_2$(lower alkyl), $—C(=O)H$, $—C(=O)$(lower alkyl), $—SO_2$(lower alkyl), $—SO_2$(amino), and $C_{1-4}$alkyl substituted with one to two of halogen, cyano, hydroxy, lower alkoxy, trifluoromethyl, trifluoromethoxy, amino, $C_{1-4}$alkylamino, amino$C_{1-4}$alkyl, $—CO_2H$, $—CO_2$(lower alkyl), $—C(=O)H$, $—C(=O)$(lower alkyl), $—SO_2$(lower alkyl), and/or $—SO_2$(amino), and is attached at any available carbon atom of the tetrahydropyrazine ring, or two $R_3$ groups attached to the same carbon atom optionally may be taken together to form a carbonyl group;

$R_4$ and $R_5$ are individually selected from hydrogen, lower alkyl, halogen, cyano, hydroxy, lower alkoxy, trifluoromethyl, trifluoromethoxy, amino, $C_{1-4}$alkylamino, amino$C_{1-4}$alkyl, $—CO_2H$, $—CO_2$(lower alkyl), $—C(=O)H$, $—C(=O)$(lower alkyl), $—SO_2$(lower alkyl), $—SO_2$(amino), and $C_{1-4}$alkyl substituted with one to two of halogen, cyano, hydroxy, lower alkoxy, trifluoromethyl, trifluoromethoxy, amino, $C_{1-4}$alkylamino, amino$C_{1-4}$alkyl, $—CO_2H$, $—CO_2$(lower alkyl), $—C(=O)H$, $—C(=O)$(lower alkyl), $—SO_2$(lower alkyl), and/or $—SO_2$(amino);

$R_6$, $R_7$, $R_8$, $R_9$ and $R_{10}$ are independently selected from hydrogen, lower alkyl, and substituted lower alkyl;

$R_{11}$ is hydrogen, cyano, or $—OR_{10}$;

m and n are each independently 0 to 6; and p is 0 to 6;

wherein each of said substituted alkyl groups are substituted with one or more substituents independently selected from hydroxyl, halo, cyano, haloalkyl, alkoxy, alkylthio, amino, alkylamino, dialkylamino, cycloalkyl, aryl, heterocyclyl, and/or heteroaryl;

wherein said substituted cycloalkyl group is substituted with one or more substituents independently selected from halo, hydroxyl, alkyl, substituted alkyl, substituted alkyl, alkoxy, amino, cyano, heterocyclyl, aryl, heteroaryl, alkylamino, and/or dialkylamino;

wherein said substituted aryl group is substituted with one or more substituents independently selected from halogen, alkyl, substituted alkyl, alkoxy, hydroxy, amino, cycloalkyl, aryl, heteroaryl, and/or cyano;

wherein said substituted heteroaryl group is substituted with one or more substituents independently selected from halo, alkyl, substituted alkyl, cyano, hydroxy, alkoxy, $—CO_2H$, $—CO_2$-alkyl, $—C(=O)$alkyl, cycloalkyl, aryl, heterocyclo, heteroaryl, amino, alkylamino, and/or dialkylamino; and wherein each of said substituted heterocyclo group is substituted with one or more substituents independently selected from alkyl, substituted alkyl, alkoxy, amino, alkylamino, dialkylamino, cyano, halo, cycloalkyl, aryl, heteroaryl, or heterocyclyl.

2. A compound according to claim 1, and/or a pharmaceutically-acceptable salt thereof, wherein:

L is $-A_1-N(H)C(=O)-A_2-$, $-A_1-C(=O)NH-A_2-$, $-A_1-C(=O)-A_2-$, $-A_1-C(=O)O-A_2-$, $-A_1-OC(=O)-A_2-$, $-A_1-C(=NR_{11})-A_2-$, $-A_1-C(=NR_{11})NH-A_2-$, $-A_1-S-A_2-$, $-A_1-NH-A_2-$, $-A_1-S(O)_2-A_2-$, $-A_1-NHS(O)_2-A_2-$, $-A_1-S(O)_2NH-A_2-$, or $-A_1-A_2-$;

$A_1$ is $—(CH_2)_m—$;

$A_2$ is $—(CF^1_2)_n—$;

$R_2$ is hydrogen, methyl, n-propyl, isopropyl, or $—(CH_2)_v(R_{20})$;

$R_{20}$ is hydroxy, methoxy, trifluoromethyl, or N-morpholinyl;

m and n are each independently 0 to 5;

p is 0 to 4; and v is 1 or 2.

3. A compound according to claim 2, and/or a pharmaceutically-acceptable salt thereof, wherein p is 0, 1, or 2.

4. A compound according to claim 1, and/or a pharmaceutically-acceptable salt thereof, wherein p is 0.

5. A compound according to claim 1, and/or a pharmaceutically-acceptable salt thereof, wherein $R_2$ is hydrogen or methyl.

6. A compound according to claim 1, and/or a pharmaceutically-acceptable salt thereof, wherein $R_4$ and $R_5$ are each hydrogen.

7. A compound according to claim 1, and/or a pharmaceutically-acceptable salt thereof, wherein:

L is selected from $-A_1-N(H)C(=O)-A_2-$, $-A_1-C(=O)NH-A_2-$, $-A_1-C(=O)-A_2-$, $-A_1-C(=O)O-A_2-$, $-A_1-OC(=O)-A_2-$, $-A_1-C(=N-CN)-A_2-$, $-A_1-C(=N-CN)NH-A_2-$, $-A_1-S-A_2-$, $-A_1-NH-A_2-$, $-A_1-S(O)_2-A_2-$, $-A_1-NHS(O)_2-A_2-$, $-A_1-S(O)_2NH-A_2-$, and $-A_1-A_2-$;

$A_1$ is $—(CH_2)_m—$;

$A_2$ is $—(CH_2)_n—$;

$R_1$ is optionally-substituted phenyl, pyridyl, or pyrimidinyl; and m and n are each independently 0 to 5.

8. A compound according to claim 1, and/or a pharmaceutically-acceptable salt thereof, wherein:

$R_1$ is hydrogen, $C_{1-6}$alkyl, substituted $C_{1-6}$alkyl, $C_{3-7}$cycloalkyl, five or six membered heterocyclo, aryl or heteroaryl, wherein each such cycloalkyl, heterocyclo, aryl or heteroaryl group in turn is optionally substituted with one to four groups as valence allows selected from halogen, lower alkyl, haloalkyl, methoxy, cyano, $SO_2$(lower alkyl), and/or phenyl, wherein said phenyl again in turn is optionally substituted with one to three groups selected from lower alkyl, halogen, trifluoromethyl, cyano, and/or trifluoromethoxy; or when L is $-A_1-A_2-$ or when m is greater than 0, $R_1$ may be cyano.

9. A compound according to claim 1, and/or a pharmaceutically-acceptable salt thereof, wherein:

L is selected from $—(CH_2)_r—$, $—S—(CH_2)_r—$, $—S(O)_2—$, $OC(=O)—$, $—C(=O)(CH_2)_r—$, $—CH_2—O—C(=O)—$, $—(CH_2)_rN(H)C(=O)—$, $—NHS(O)_2—$, $—S(O)_2NH—$, and $—C(=NCN)NH—$ wherein r is 0 to 6.

10. A compound according to claim 1, and/or a pharmaceutically-acceptable salt thereof, wherein:

L is selected from a bond, —N(H)C(=O)—, and —OC(=O).

11. A compound according to claim 1, and/or a pharmaceutically-acceptable salt thereof, wherein:

Ar is

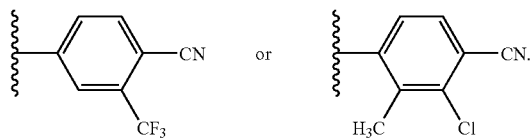

12. A compound according to claim 1, and/or a pharmaceutically-acceptable salt thereof, having the formula (Ia),

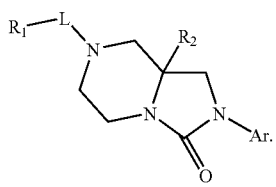

(Ia)

13. A compound according to claim 12, and/or a pharmaceutically-acceptable salt thereof, wherein:

$R_1$ is hydrogen, $C_{1-6}$alkyl, substituted $C_{1-6}$alkyl, $C_{3-7}$cycloalkyl, five or six membered heterocyclo, aryl or heteroaryl, wherein each such cycloalkyl, heterocyclo, aryl or heteroaryl group in turn is optionally substituted with one to four groups as valence allows selected from halogen, lower alkyl, haloalkyl, methoxy, cyano, $SO_2$(lower alkyl), and/or phenyl, wherein said phenyl again in turn is optionally substituted with one to three groups selected from lower alkyl, halogen, trifluoromethyl, cyano, and/or trifluoromethoxy; or when L is -$A_1$-$A_2$- or when m is greater than 0, $R_1$ may be cyano.

14. A compound according to claim 13, and/or a pharmaceutically-acceptable salt thereof, wherein:

L is selected from —(CH$_2$)$_r$—, —S—(CH$_2$)$_r$—, —S(O)$_2$—, —CO(=O)—, —C(=O)(CH$_2$)$_r$—, —CH$_2$—O—C(=O)—, —(CH$_2$)$_r$N(H)C(=O)—, —NHS(O)$_2$—, —S(O)$_2$NH—, and —C(=NCN)NH— wherein r is 0 to 6.

15. A pharmaceutical composition comprising a compound according to claim 1 and a pharmaceutically-acceptable carrier or diluent.

16. The compound according to claim 1, and/or a pharmaceutically-acceptable salt thereof, wherein $R_{15}$ is cyano.

17. The compound according to claim 1 and/or a pharmaceutically-acceptable salt thereof, wherein said compound is:

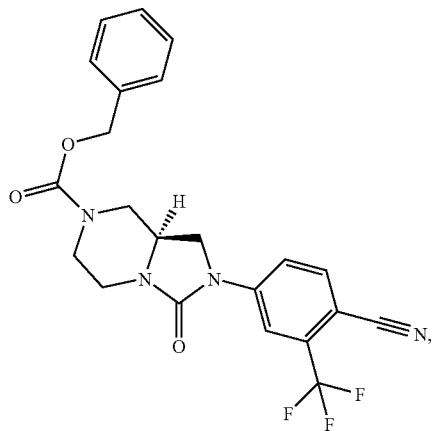

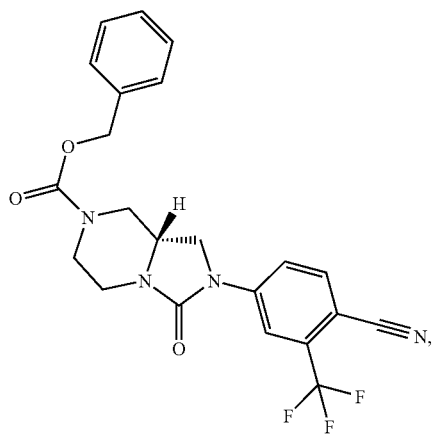

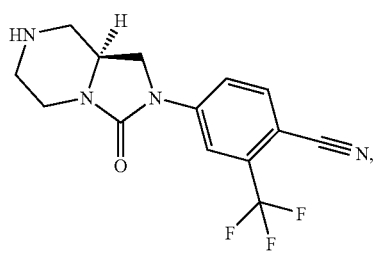

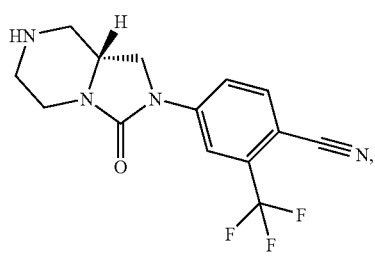

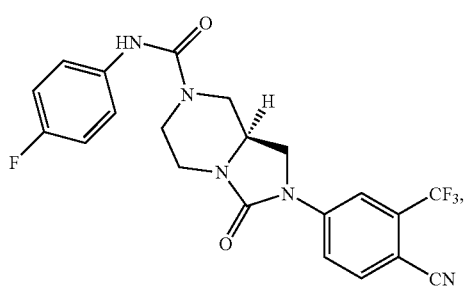

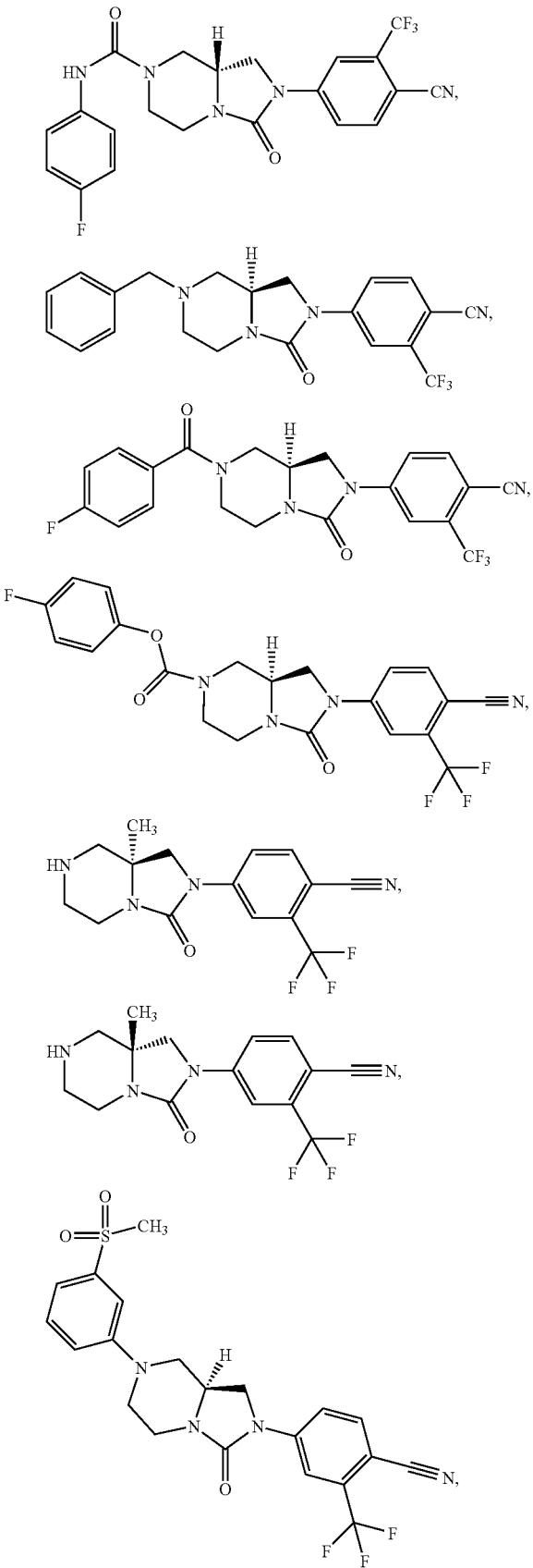
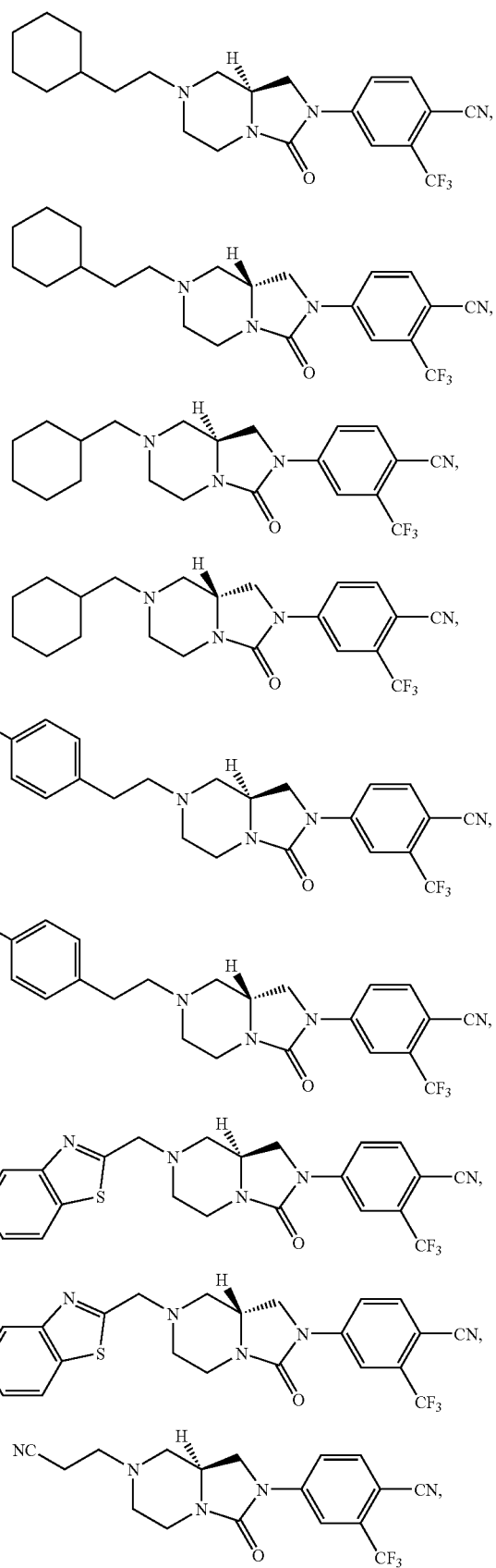

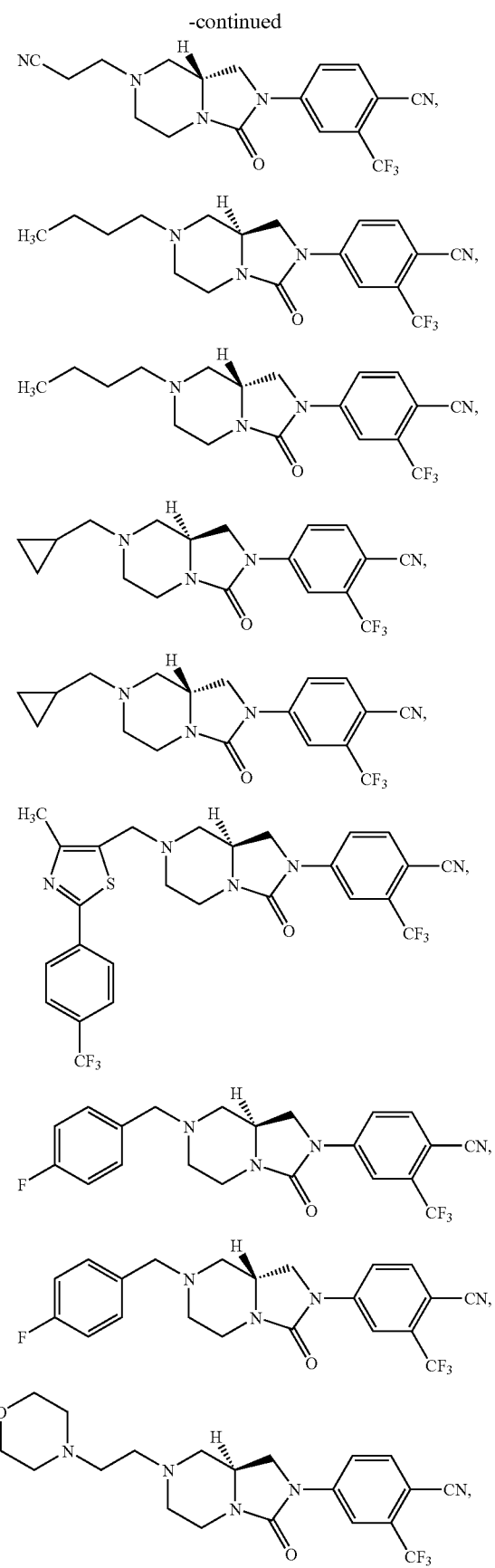
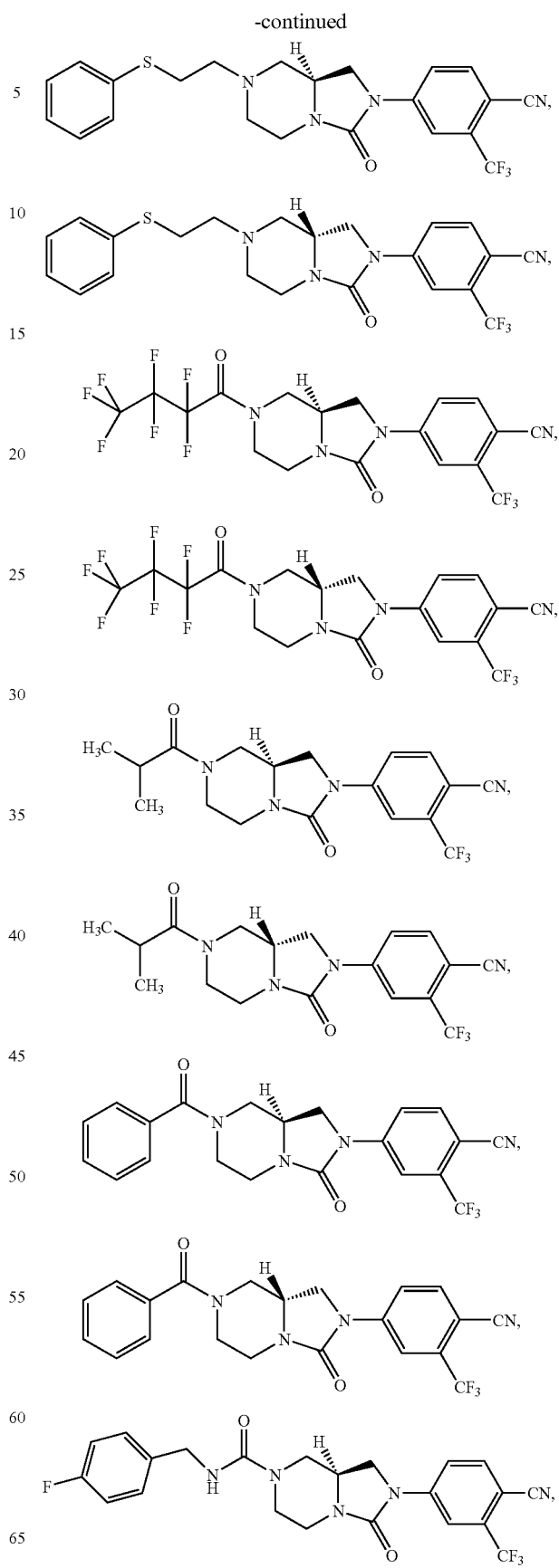

73
-continued
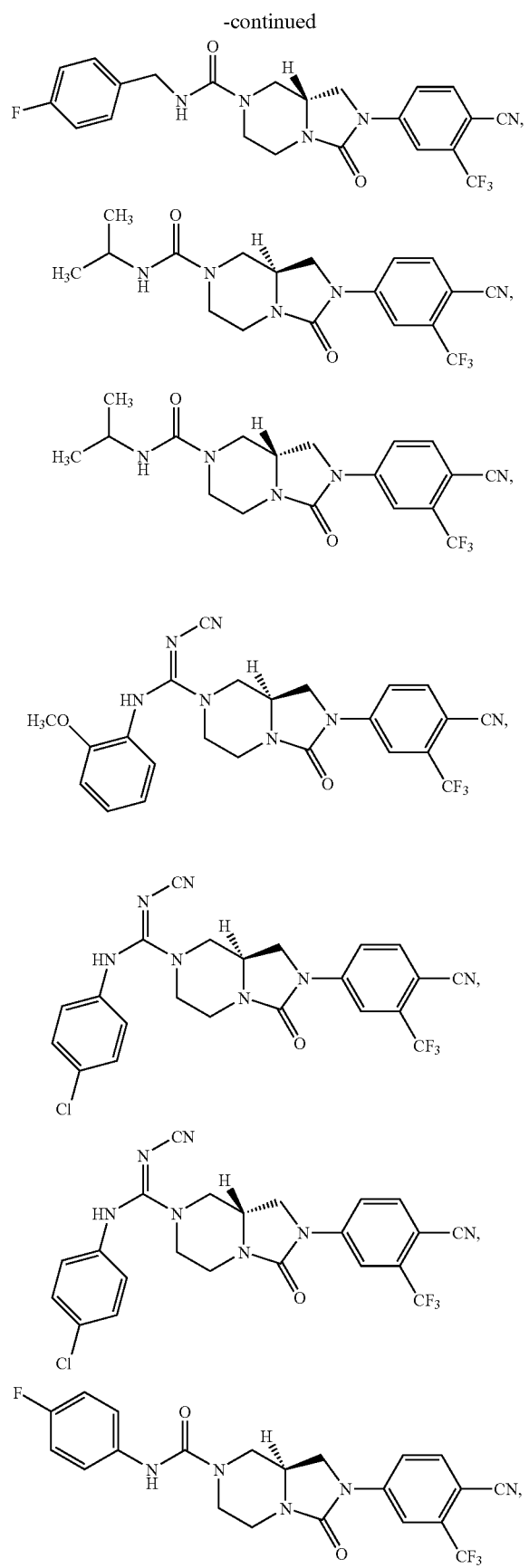
74
-continued
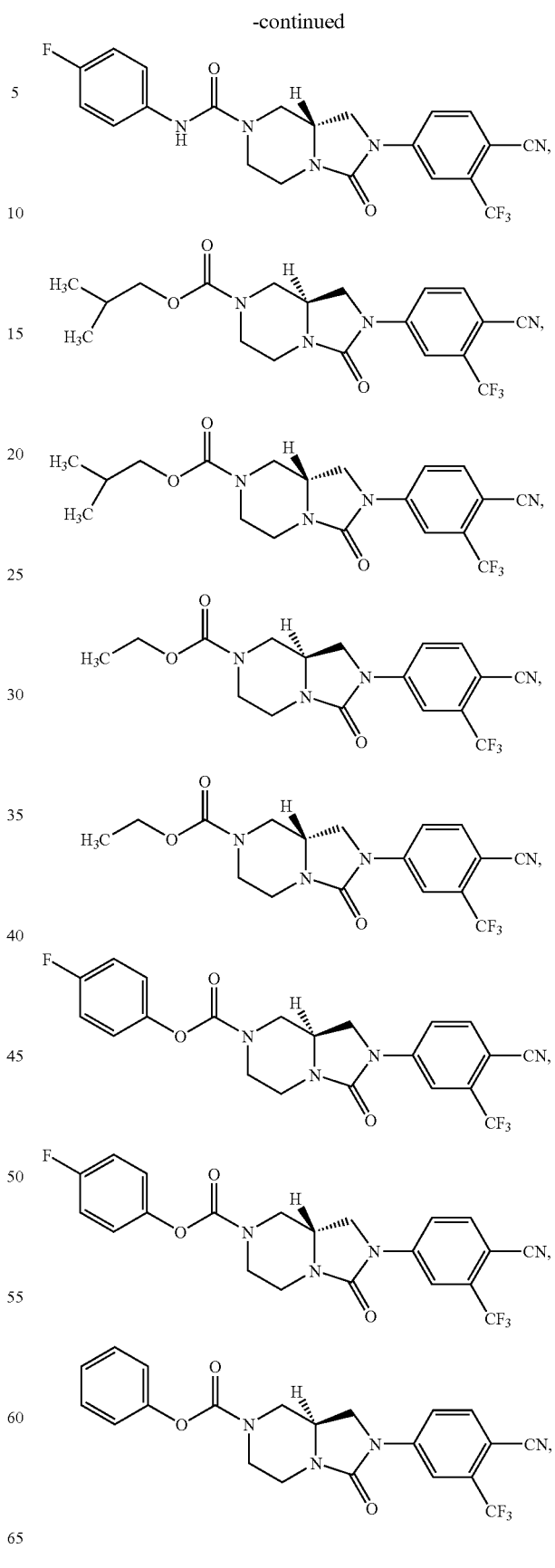

-continued
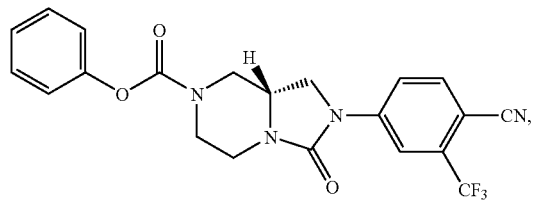
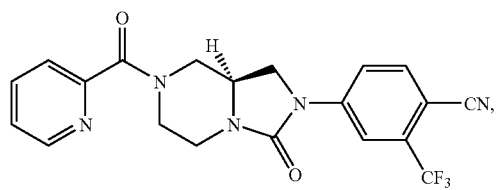
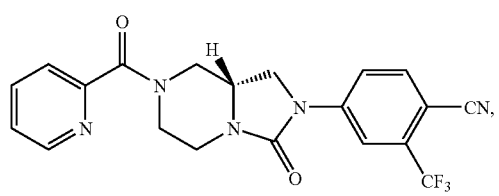
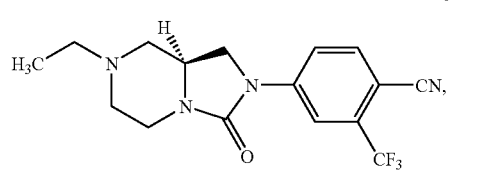
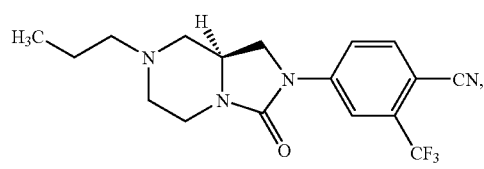
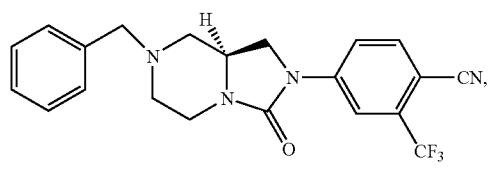
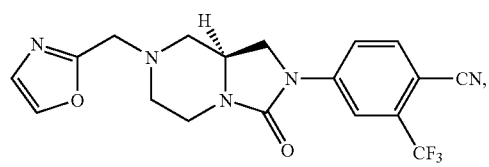
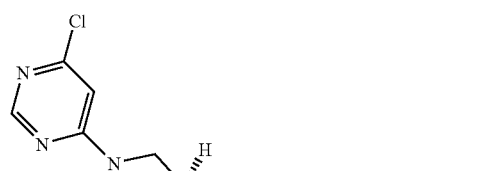
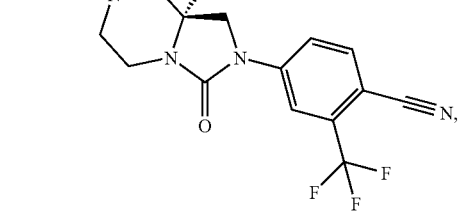
-continued
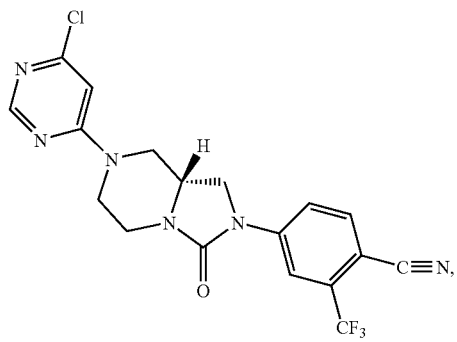
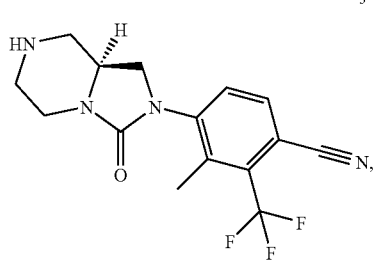
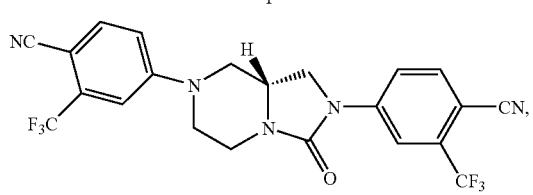
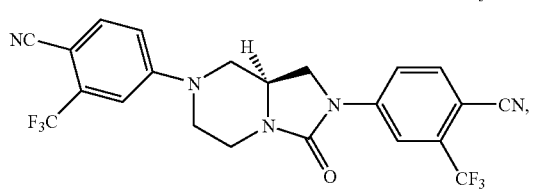
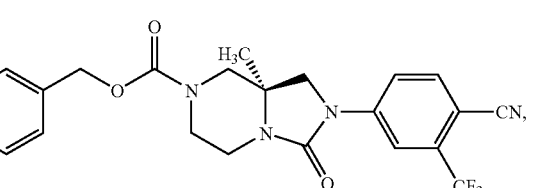
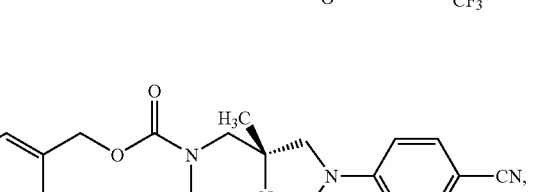
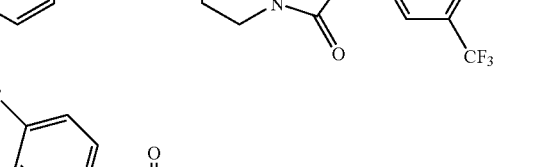
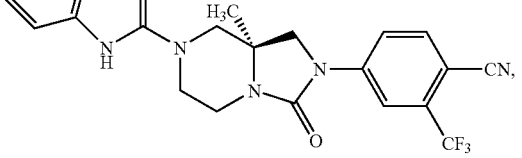

77
-continued
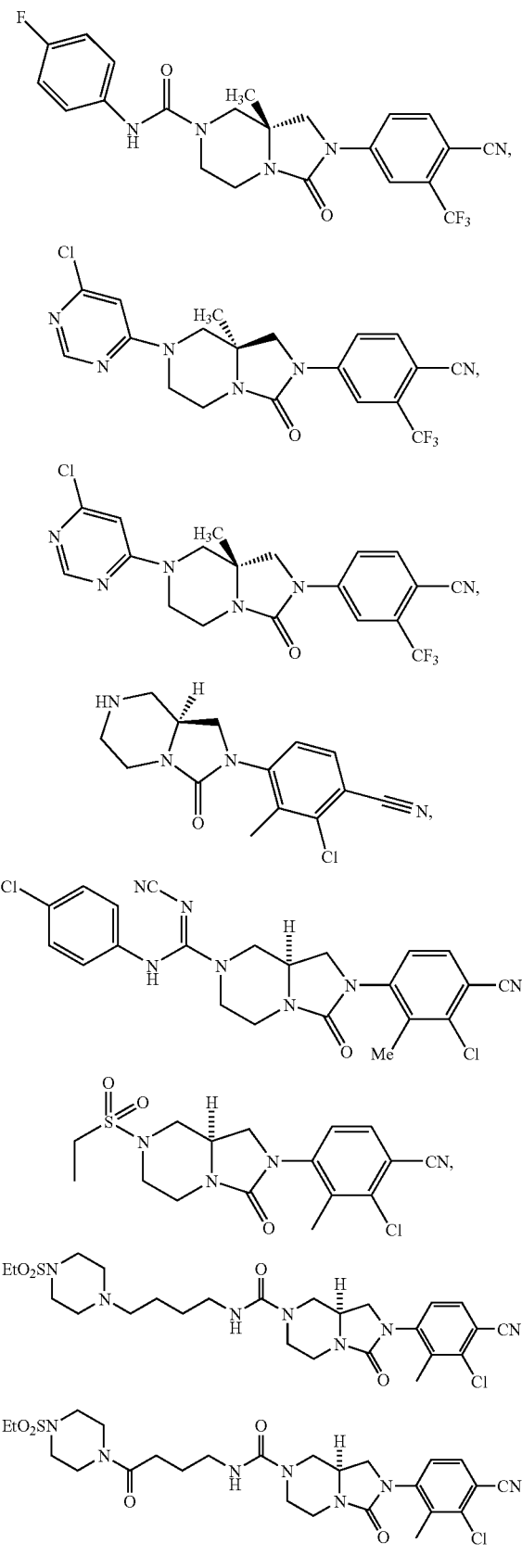
78
-continued
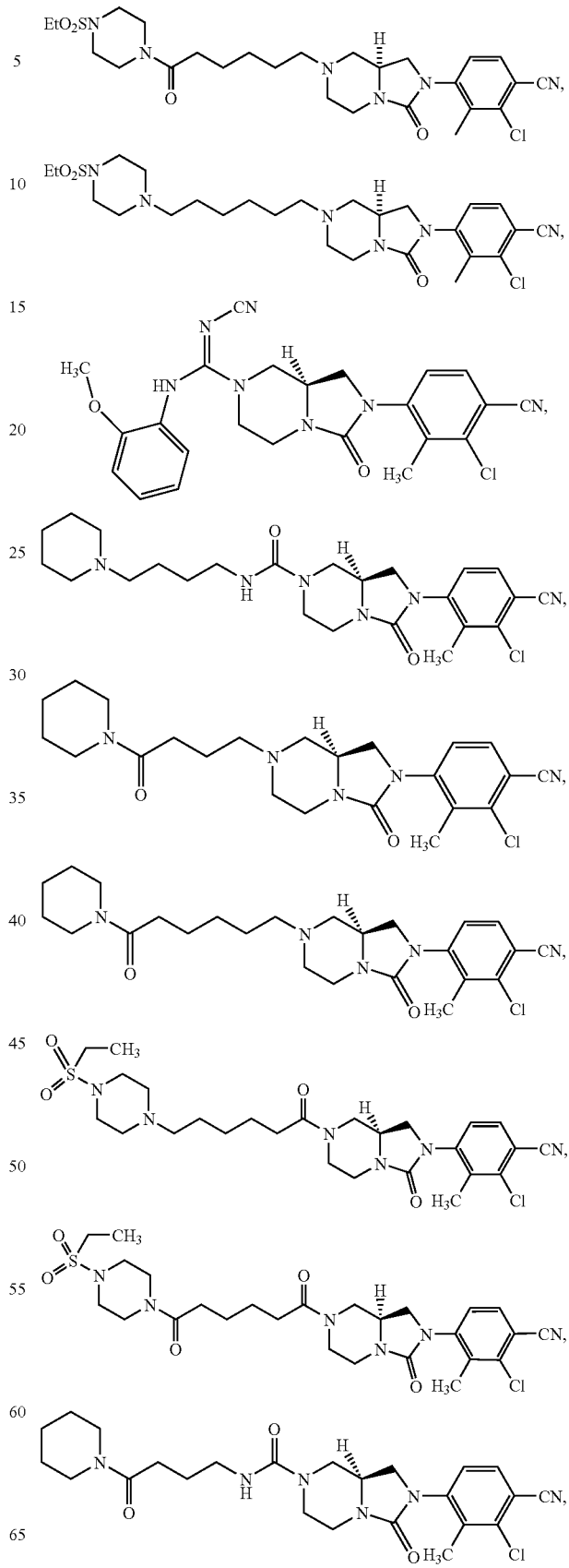

-continued
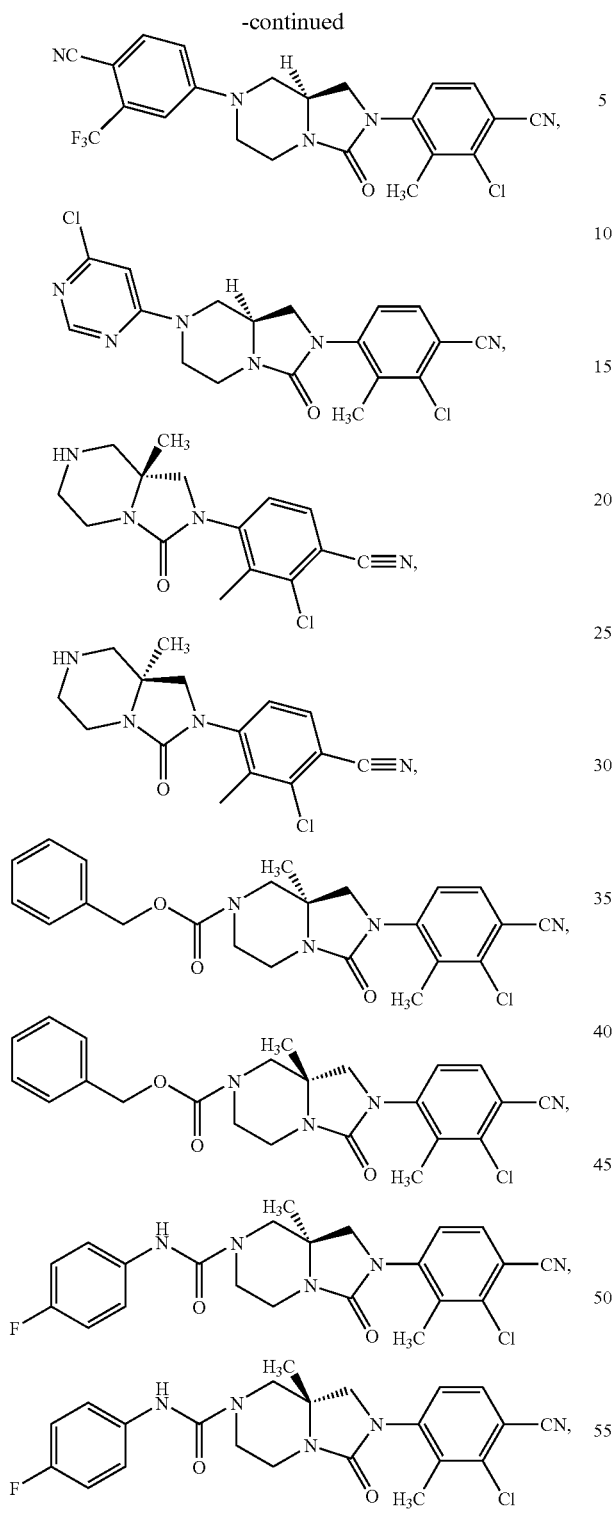
-continued
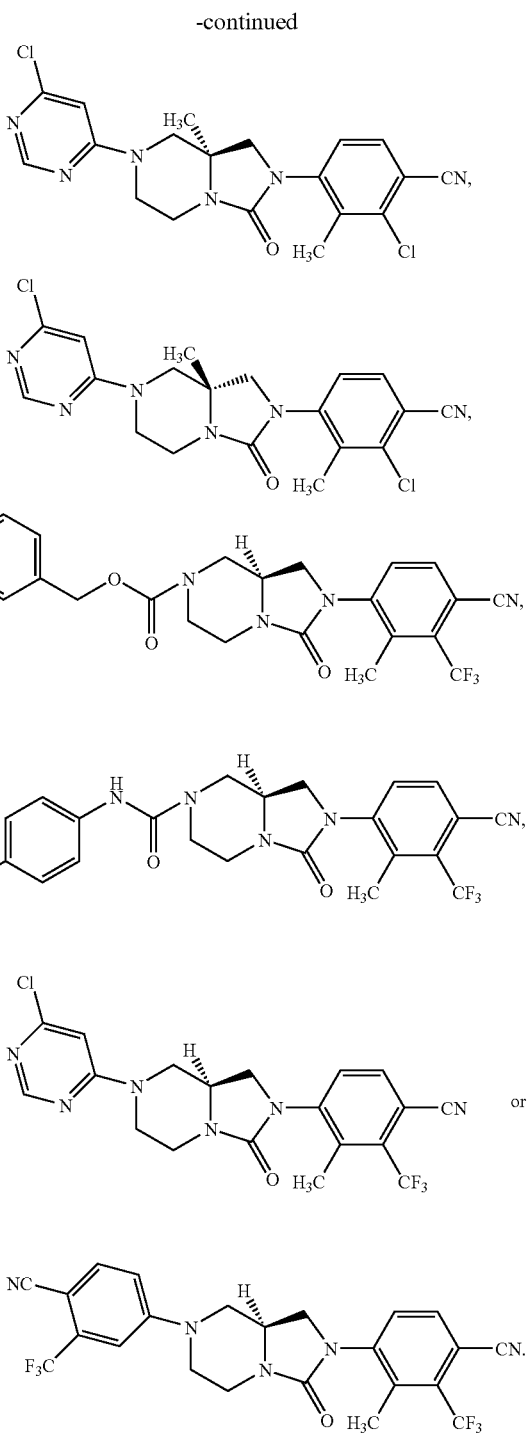
or
* * * * *

UNITED STATES PATENT AND TRADEMARK OFFICE
CERTIFICATE OF CORRECTION

| | | |
|---|---|---|
| PATENT NO. | : 7,776,859 B2 | Page 1 of 1 |
| APPLICATION NO. | : 11/546965 | |
| DATED | : August 17, 2010 | |
| INVENTOR(S) | : James Balog et al. | |

It is certified that error appears in the above-identified patent and that said Letters Patent is hereby corrected as shown below:

On the Title page:
Abstract, line 3

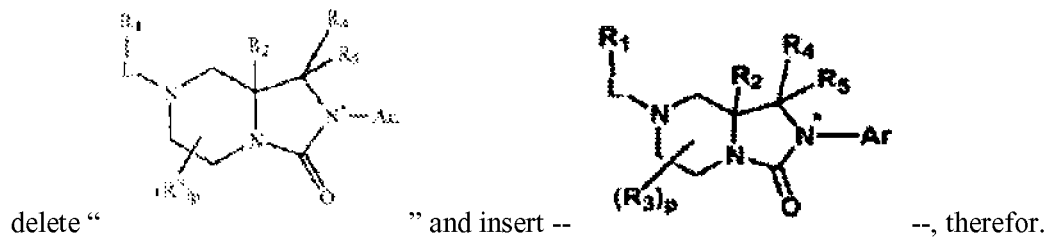

delete " " and insert -- --, therefor.

In the Claims:

Claim 1, col. 65, line 4, delete "$R_{14}$" and insert -- $R_{14}$, -- , therefor;

Claim 2, col. 66, line 16, delete "—$(CF^1_2)_n$—;" and insert -- —$(CH_2)_n$—; --, therefor;

Claim 9, col. 66, line 64, delete "OC(=O)—," and insert -- —OC(=O)—, --, therefor; and Claim 17, col. 78, line 55, delete "                                                                            "
and insert --                                                                            --, therefor.

Signed and Sealed this
Fifteenth Day of February, 2011

David J. Kappos
*Director of the United States Patent and Trademark Office*